US011298020B2

(12) United States Patent
Markel

(10) Patent No.: US 11,298,020 B2
(45) Date of Patent: *Apr. 12, 2022

(54) MOBILE COMMUNICATION DEVICE AND OTHER DEVICES WITH CARDIOVASCULAR MONITORING CAPABILITY

(71) Applicant: Gal Markel, Haifa (IL)

(72) Inventor: Gal Markel, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,337

(22) Filed: Sep. 27, 2016

(65) Prior Publication Data

US 2017/0143205 A1 May 25, 2017

Related U.S. Application Data

(63) Continuation of application No. 11/492,278, filed on Jul. 25, 2006, now Pat. No. 9,451,895.

(Continued)

(51) Int. Cl.
*A61B 5/00* (2006.01)
*A61B 5/0408* (2006.01)
(Continued)

(52) U.S. Cl.
CPC .......... *A61B 5/0022* (2013.01); *A61B 5/0006* (2013.01); *A61B 5/25* (2021.01);
(Continued)

(58) Field of Classification Search
CPC .... A61N 2560/0462; A61N 2560/0468; A61B 5/0404; A61B 5/6887; A61B 5/0022;
(Continued)

(56) References Cited

U.S. PATENT DOCUMENTS

| | | | |
|---|---|---|---|
| 4,086,916 | A | 5/1978 | Freeman et al. |
| 5,465,727 | A | 11/1995 | Reinhold, Jr. |

(Continued)

FOREIGN PATENT DOCUMENTS

| | | |
|---|---|---|
| EP | 1407713 A1 | 4/2004 |
| WO | 03094720 | 11/2003 |

OTHER PUBLICATIONS

Int'l Preliminary Report on Patentability Appln. No. PCT/IB2006/003654 dated Jun. 4, 2019.

(Continued)

*Primary Examiner* — Jennifer Pitrak McDonald
*Assistant Examiner* — Pamela M. Bays
(74) *Attorney, Agent, or Firm* — McAndrews, Held & Malloy, Ltd.

(57) ABSTRACT

A general-purpose mobile communication device, general-purpose computer user-interface device, and other non-health-related electronic devices with cardiovascular monitoring capability. Various aspects of the present invention may comprise a general-purpose mobile communication device (e.g., a cellular telephone, portable email device, personal digital assistant, etc.) comprising a communication interface module adapted to communicate with a general-purpose communication network, and at least one module operational to acquire cardiac information from a user of the general-purpose mobile communication device. The general-purpose communication device may, for example, comprise a cardiac sensor (e.g., electrodes) disposed on the mobile communication device, which may be utilized to acquire cardiac information during use of the mobile communication device. Various aspects of the present invention may also comprise a non-health related electronic device (e.g., a general-purpose mobile communication device, general-purpose user-interface device for a general-purpose (Continued)

computer, gaming controller, etc.) that, during normal non-health-related utilization, acquire, analyze and/or communicate user health-related information.

17 Claims, 24 Drawing Sheets

Related U.S. Application Data

(60) Provisional application No. 60/702,148, filed on Jul. 25, 2005.

(51) Int. Cl.
*H04M 1/725* (2021.01)
*A61B 5/25* (2021.01)
*A61B 5/332* (2021.01)
*H04M 1/72421* (2021.01)

(52) U.S. Cl.
CPC ............ *A61B 5/332* (2021.01); *A61B 5/6887* (2013.01); *A61B 5/6815* (2013.01); *A61B 5/6838* (2013.01); *A61B 5/6898* (2013.01); *A61B 5/7475* (2013.01); *A61B 2503/22* (2013.01); *A61B 2560/0462* (2013.01); *A61B 2560/0468* (2013.01); *H04M 1/72421* (2021.01)

(58) Field of Classification Search
CPC ... A61B 5/6898; A61B 5/0006; A61B 5/0408; A61B 5/7475; A61B 2560/0462; A61B 2560/0468; A61B 5/25; A61B 5/332; A61B 2503/22
USPC ......................... 600/508, 509, 518, 520, 301
See application file for complete search history.

(56) References Cited

U.S. PATENT DOCUMENTS

| | | | |
|---|---|---|---|
| 6,073,046 A | 6/2000 | Patel et al. | |
| 6,219,408 B1 | 4/2001 | Kurth | |
| 6,264,614 B1 | 7/2001 | Albert et al. | |
| 6,485,416 B1* | 11/2002 | Platt | A61B 5/0006 128/904 |
| 6,494,830 B1* | 12/2002 | Wessel | A61B 5/04325 273/459 |
| 6,546,232 B1 | 4/2003 | Sack et al. | |
| 7,117,031 B2 | 10/2006 | Lohman et al. | |
| 9,451,895 B2 | 9/2016 | Markel | |
| 2001/0039372 A1* | 11/2001 | Yasushi | G16H 40/63 600/300 |
| 2002/0115435 A1 | 8/2002 | Soh | |
| 2003/0009088 A1 | 1/2003 | Korth et al. | |
| 2003/0050731 A1 | 3/2003 | Rosenblum | |
| 2003/0167149 A1 | 9/2003 | Simon | |
| 2003/0212311 A1* | 11/2003 | Nova | A61N 1/37258 600/300 |
| 2004/0044293 A1* | 3/2004 | Burton | A61B 5/18 600/544 |
| 2004/0046666 A1* | 3/2004 | Yasuchi | A61B 5/02405 340/573.1 |
| 2004/0152957 A1 | 8/2004 | Stivoric et al. | |
| 2004/0215091 A1* | 10/2004 | Lohman | A61B 5/046 600/515 |
| 2005/0239493 A1* | 10/2005 | Batkin | A61B 5/0404 455/550.1 |
| 2006/0058697 A1 | 3/2006 | Mochizuki et al. | |
| 2006/0224072 A1 | 10/2006 | Shennib | |

OTHER PUBLICATIONS

Written Opinion of the Int'l Searching Authority Appln. No. PCT/IB2006/003654 dated May 24, 2019.
Extended European Search Report EP Appln No. 06831736.1 dated Sep. 10, 2020.

* cited by examiner

MOBILE COMMUNICATION DEVICE AND OTHER DEVICES WITH CARDIOVASCULAR MONITORING CAPABILITY

CROSS-REFERENCE TO RELATED APPLICATIONS/INCORPORATION BY REFERENCE

The present application is a continuation of co-pending U.S. patent application Ser. No. 11/492,278, filed Jul. 25, 2006, that issued as U.S. Pat. No. 9,451,895 on Sep. 27, 2016, and which claims priority from U.S. Provisional Patent Application Ser. No. 60/702,148, filed Jul. 25, 2005, and titled "Mobile Communication Device and Other Devices with Cardiovascular Monitoring Capability," the contents of which are hereby incorporated herein by reference, in their entirety.

FEDERALLY SPONSORED RESEARCH OR DEVELOPMENT

[Not Applicable]

SEQUENCE LISTING

[Not Applicable]

MICROFICHE/COPYRIGHT REFERENCE

[Not Applicable]

BACKGROUND OF THE INVENTION

A substantial portion of cardiovascular problems exhibit detectable symptoms. In various scenarios where an individual is being monitored, medical assistance may be obtained based on monitored heart beat characteristics before a particular heart problem becomes fatal.

Present cardiovascular monitoring systems are cumbersome and inconvenient. Additionally, in most fatal incidents involving various cardiovascular pathologies, the individual had no prior knowledge of any cardiac issues that would have caused the individual to seek medical assistance and possibly obtain dedicated heart monitoring apparatus.

Further limitations and disadvantages of conventional and traditional approaches will become apparent to one of skill in the art, through comparison of such systems with the present invention as set forth in the remainder of the present application with reference to the drawings.

BRIEF SUMMARY OF THE INVENTION

Various aspects of the present invention provide a mobile communication device, general-purpose computer user interface device, and other electronic devices with cardiovascular monitoring capability.

These and other advantages, aspects and novel features of the present invention, as well as details of illustrative aspects thereof, will be more fully understood from the following description and drawings.

DETAILED DESCRIPTION OF THE INVENTION

Figure 1:
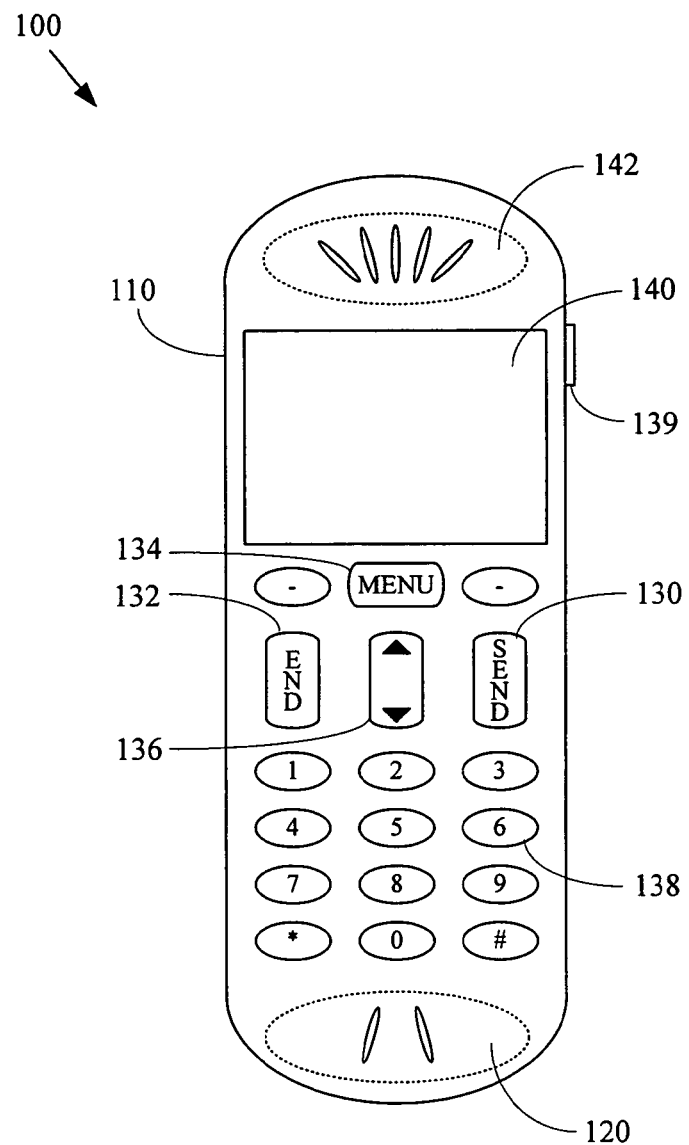
FIG. 1 is a diagram illustrating an exemplary mobile communication device, in accordance with various aspects of the present invention.

FIG. 1 is a diagram illustrating an exemplary mobile communication device 100 in accordance with various aspects of the present invention. The mobile communication device 100 may comprise characteristics of any of a large variety of mobile communication devices (e.g., general-purpose mobile communication devices). For example and without limitation, the mobile communication device 100 may comprise characteristics of a cellular or portable telephone. The mobile communication device 100 may, for example, comprise characteristics of a personal digital assistant with mobile communication capability, portable email device, pager, etc. The scope of various aspects of the present invention should not be limited by characteristics of any particular mobile communication device (e.g., a general-purpose mobile communication device).

The exemplary mobile communication device 100 ("MCD") may comprise a main body portion 110. The MCD 100 may also comprise various user input features, for example, a microphone 120 and various pushbuttons. Such pushbuttons may, for example and without limitation, comprise a send button 130, an end button 132, a menu button 134, a scroll button 136, a numeric button 138 and a volume control button 139. The MCD 100 may also comprise various user output features, for example, a display 140 (which may also function as a touch screen input feature) and a speaker 142. Various input and output features of the exemplary MCD 100 will be discussed below. It should be recognized that various aspects of the present invention should not be limited by characteristics of the particular user input and output features illustrated in FIG. 1. Various aspects of the present invention are readily extensible to other MCD features.

The exemplary mobile communication device 100 may comprise at least one cardiac sensor (e.g., one or more electrodes, an audio monitoring or acoustical detection device, etc.) that is adapted to detect cardiac activity of a user of the MCD 100. Such electrodes may, for example, be adapted to detect cardiac activity of a user that is conductively coupled to the electrodes (e.g., by touching the electrodes). Such electrodes may be incorporated into the MCD 100 in any of a variety of manners. The following discussion will present various exemplary electrode placements.

The following discussion will generally discuss cardiac sensing electrodes. Note, however, that various aspects of the present invention also apply to other cardiac sensors (e.g., audio monitoring devices). In a non-limiting exemplary scenario, the microphone 120 of the mobile communication device 100 may be utilized as a cardiac sensor. In another non-limiting exemplary scenario, an audio sensor or detector may be disposed in any of a number of locations of the mobile communication device 100, examples of which will be provided in the following electrode placement discussion.

Electrodes may generally comprise conductive material. For example, an electrode may comprise a metallic surface exposed for user contact. Also for example, an electrode may be formed from conductive plastic (or another material) that may be integrated into various molded components of the mobile communication device. For example, various conductive plastics (e.g., graphite-impregnated plastic or the like) may provide sufficient conductivity for an electrode to perform adequately. It should be recognized that the scope of various aspects of the present invention should not be limited by characteristics of particular electrodes or electrode placements.

Electrodes (or other sensors) may be shaped, positioned or formed with various physical features to enhance collection of cardiovascular information from a user. For example and without limitation, an electrode may comprise one or more projections to enhance conductive contact with a user. Also, an electrode may comprise one or more depressions or indentations to enhance conductive contact with a user.

Figure 3:
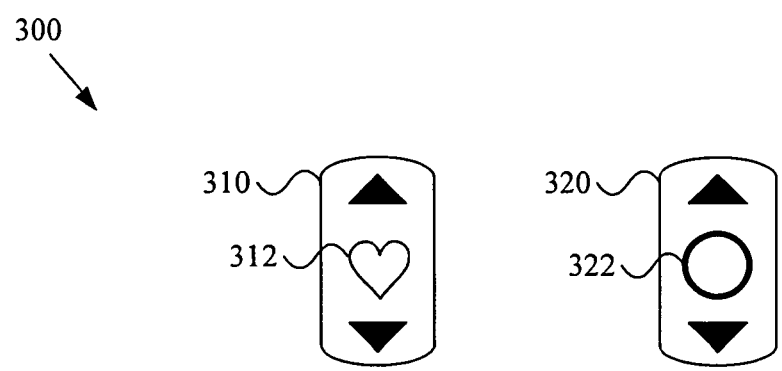
FIG. 3 is a block diagram illustrating exemplary electrodes, in accordance with various aspects of the present invention.

Electrodes may also be identified for the user in any of a variety of manners or may be generally concealed from the user. For example and without limitation, as provided in non-limiting examples in FIG. 3, an electrode may comprise a visible or tactile indicium to indicate the location of the electrode to a user. For example, the first pushbutton 310 comprises a heart-shaped indium 312 (or other visible characteristic) to notify a user of the location of the electrode and also the function of the electrode. Also for example, the second pushbutton 320 comprises a circular projection (or other tactile characteristic) to notify a user of the location of the electrode. In general, the location and/or function of an electrode may be identified to a user in any of variety of manners.

As mentioned above, in various non-limiting configurations, an electrode (or all electrodes) or other sensor may be substantially concealed (or hidden) from a user. For example and without limitation, an electrode may comprise molded conductive plastic with little or no visible indication of the electrode presence. In various exemplary scenarios, a user need not be aware of the presence of the electrode.

In general, one or more electrodes (or other sensors) may be positioned such that the one or more electrodes contact a user during normal (or typical) use of the MCD 100. Such normal use may, for example, comprise talking on a telephone, reading messages, perusing a phone book, typing a message, initiating a phone call, sending an email message, entering information in a notepad, etc.).

For example, an electrode (or other sensor) may be disposed on a pushbutton of the MCD 100. As illustrated in FIG. 1, an electrode may be disposed on any, any combination of, or all of alphanumeric pushbuttons (e.g., pushbutton 138), a send button 130, an end button 132, a menu button 134, a scroll button 136 (or other cursor moving feature, for example, a touch pad, thumbwheel, track ball, eraser tip controller, etc.), a volume control button 139 (or other volume-control feature), etc. Such electrode placement may, for example, provide for electrode contact with a user while the user is pushing a particular one or more pushbuttons.

Also for example, an electrode (or other sensor) may be placed on a main body portion 110 of the MCD 100. For example, such a main body portion 110 may comprise the portion of the MCD 100 that is generally held in the hand during normal use of the MCD 100. As will be shown in later figures, one or more electrodes may be placed on side or rear portions of the main body portion 100. Such placement may, for example, provide for electrode contact with a user's hand during use of the MCD 100.

Further for example, an electrode (or other sensor) may be placed on (or proximate to) an audio output portion 142 (e.g., a speaker) of the MCD 100. Such a placement may, for example, provide for electrode contact with an ear or cheek of a user of the MCD 100. Also for example, an electrode may be disposed on a video display device 140 (e.g., a border of the display or integrated into a touch screen).

Figure 4:
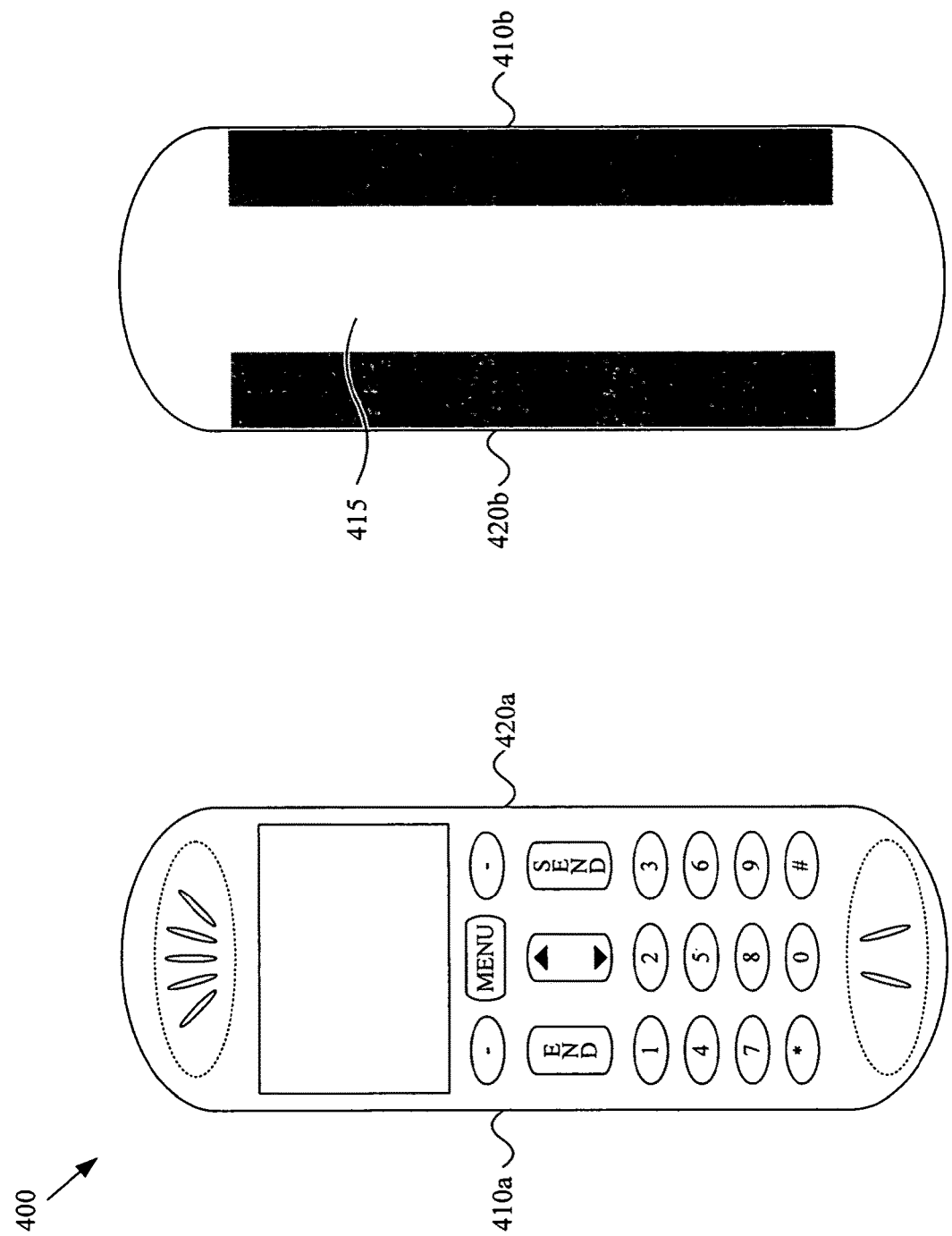
FIG. 4 is a diagram illustrating an exemplary mobile communication device, in accordance with various aspects of the present invention.

A plurality of electrodes (or other sensors) may be disposed in any of a variety of locations, non-limiting examples of dual-electrode placement will now be presented. For example, first and second electrodes may be disposed on a main body portion 110 of the MCD 100. FIG. 4 provides a non-limiting example of such electrode placement. The mobile communication device 400 illustrated in FIG. 4 may comprise a left side portion 410 and a right side portion 420. A first electrode may, for example, be placed on the left side portion 410 (e.g., placed on or molded into region 410$b$), and a second electrode may, for example, be placed on the right side portion 420 (e.g., placed on or molded into region 420$b$). In various exemplary configurations (e.g., where regions 410$b$ and 420$b$ include conductive plastic), an insulating region 415 may separate regions 410$b$ and 420$b$.

Figure 5:
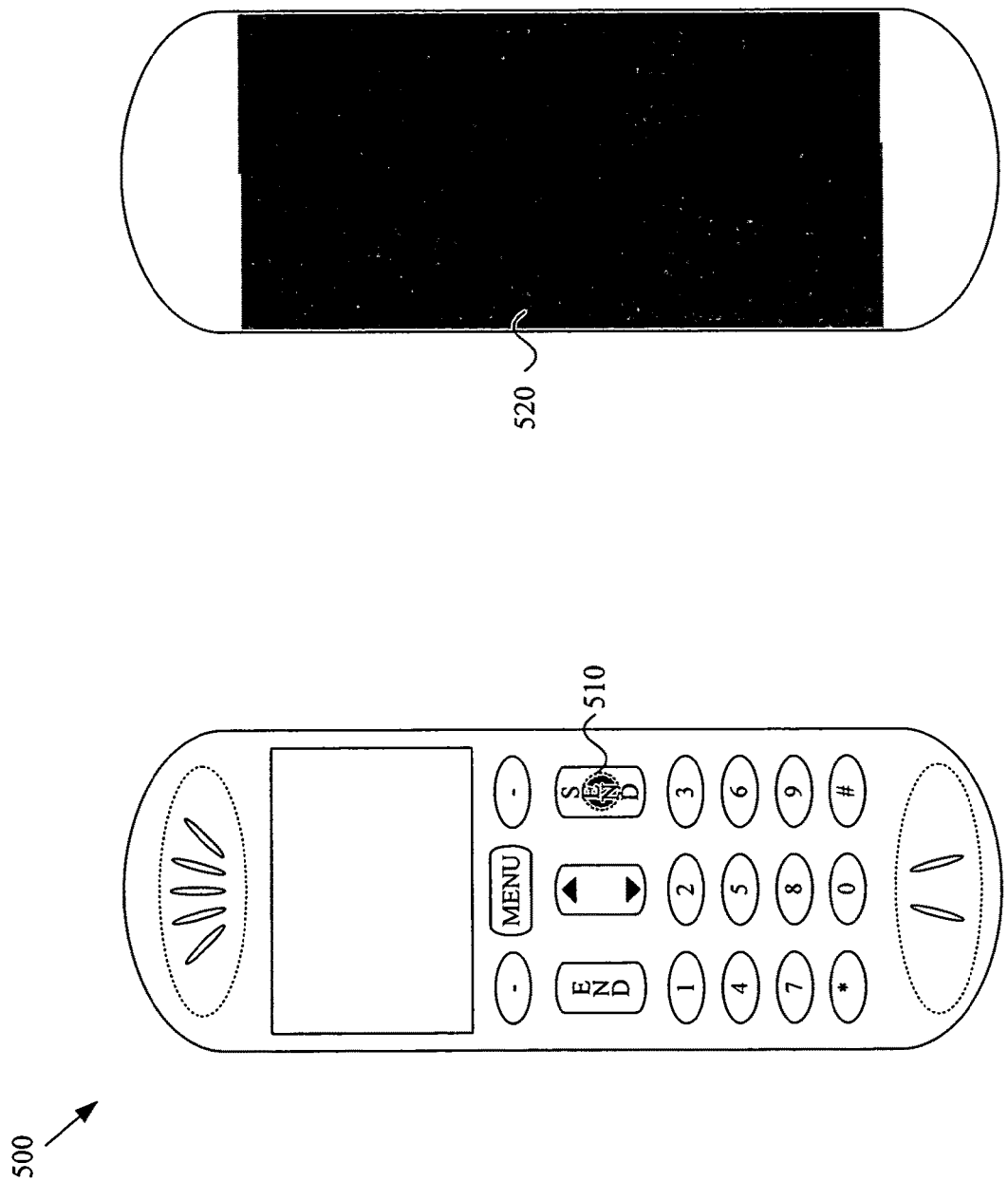
FIG. 5 is a diagram illustrating an exemplary mobile communication device, in accordance with various aspects of the present invention.

In another exemplary configuration, electrodes may be disposed on a main body portion 110 of the MCD 100 and a pushbutton (e.g., 130, 132, 134, 136, 138 and 139) of the MCD 100. FIG. 5 provides a non-limiting example of such electrode placement. The mobile communication device 500 illustrated in FIG. 5 may comprise a first electrode 510 positioned on a send button, and a second electrode disposed on the back 520 of the mobile communication device 500.

Figure 2:
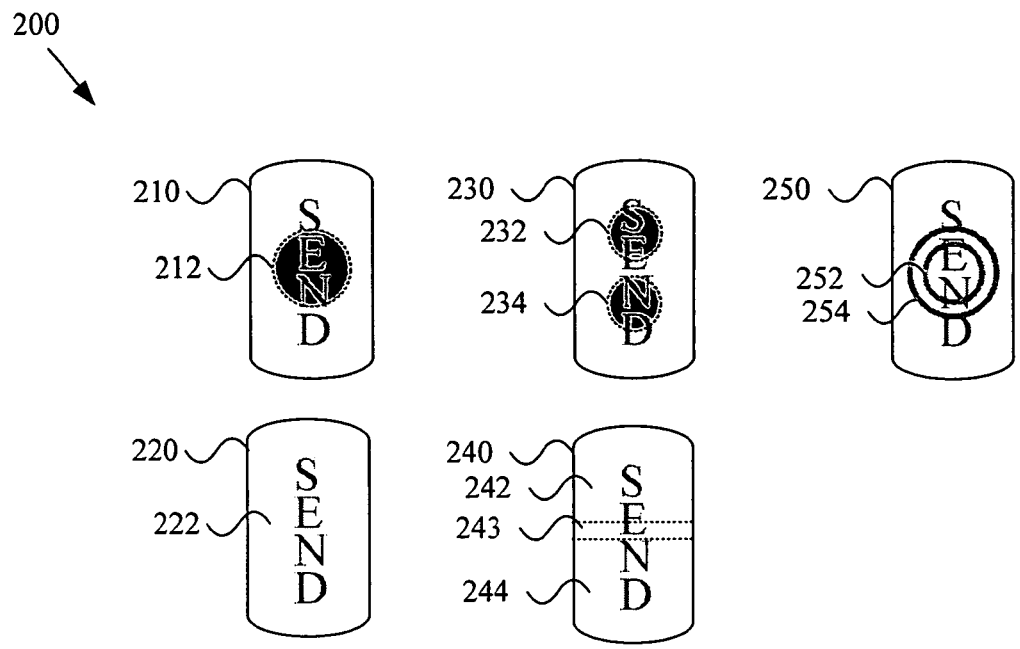
FIG. 2 is a block diagram illustrating exemplary electrodes, in accordance with various aspects of the present invention.

In yet another exemplary configuration, electrodes may be disposed on a same pushbutton of the mobile communication device 100. In such an exemplary configuration, a user may, for example, contact both electrodes while operating the pushbutton. FIG. 2 provides non-limiting examples of such placement. A first exemplary pushbutton 210 comprises a single electrode 212 (e.g., metallic or conductive plastic) disposed on the pushbutton 210. An entire second exemplary pushbutton 220 may serve as an electrode. For example, such a pushbutton 220 may be metallic or may be molded from conductive plastic. A third exemplary pushbutton 230 comprises a first electrode 232 and a second electrode 234 disposed on the exemplary pushbutton 230. A fourth exemplary pushbutton 240 comprises a first electrode 242 (e.g., a first conductive plastic region) and a second electrode 244 (e.g., a second conductive plastic region) separated by an insulating portion 243 (e.g., non-conductive plastic). A fifth exemplary pushbutton 250 comprises a first electrode 252 and a second electrode 254 shaped and disposed as concentric rings on the exemplary pushbutton 250.

It should be recognized that the exemplary pushbuttons 210-250 illustrated in FIG. 2 are merely exemplary, and accordingly, the scope of various aspects of the present invention should not be limited by particular characteristics of the exemplary pushbuttons 210-250.

In another non-limiting exemplary configuration, a first electrode may be disposed on a first pushbutton of the MCD 100, and a second electrode may be disposed on a second pushbutton of the MCD 100. Such placement may, for example, provide for a user to be generally contacting at least one of the first and second electrodes during use of a keypad. Also such placement may, for example, provide for convenient access for a user to contact both the first and second electrodes simultaneously (e.g., with different hands or different fingers).

Figure 6:
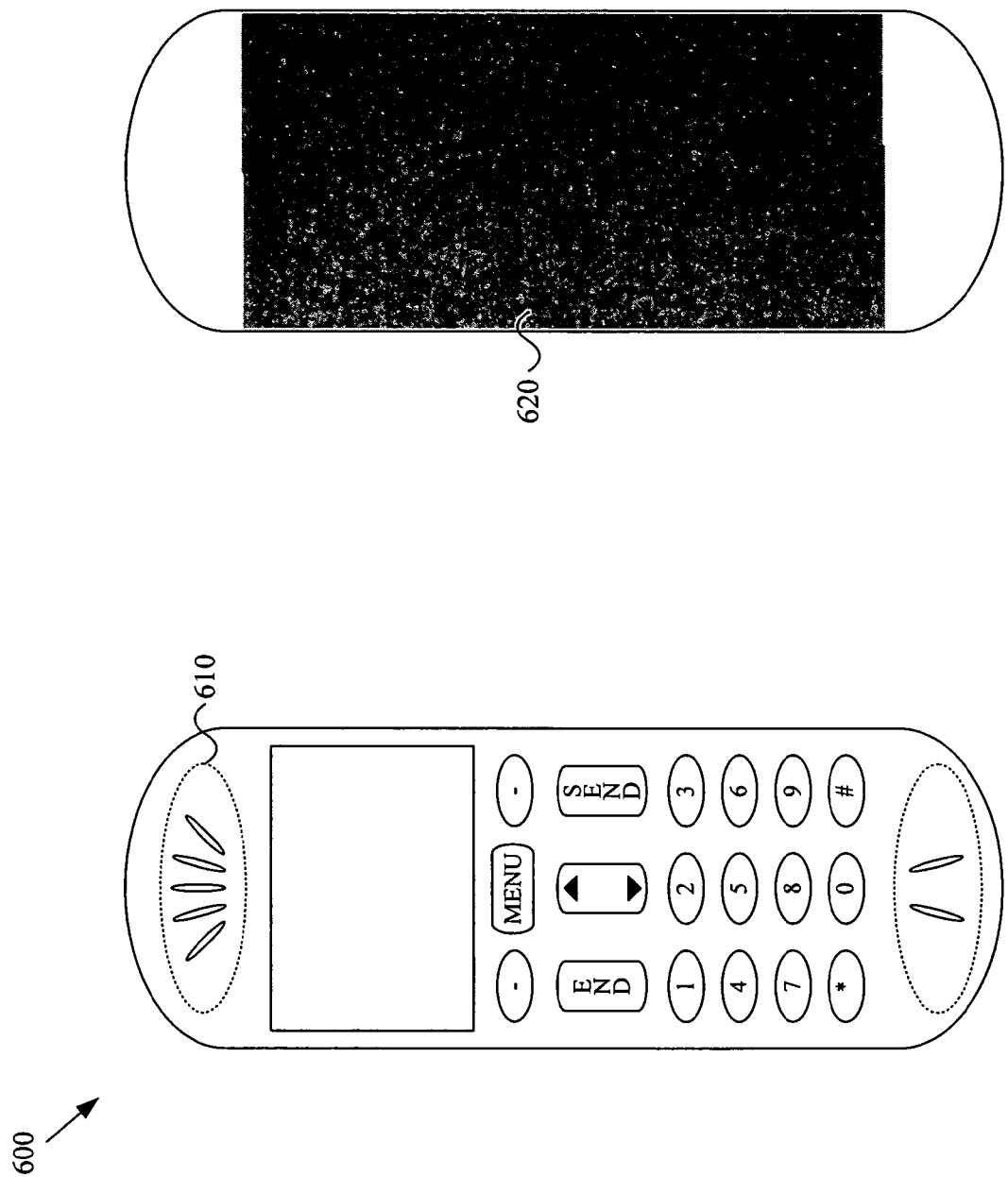
FIG. 6 is a diagram illustrating an exemplary mobile communication device, in accordance with various aspects of the present invention.

In a further non-limiting exemplary configuration, a first electrode may be disposed on a handheld portion of the MCD 100, and a second electrode may be disposed on (or proximate) an earpiece of the MCD 100. FIG. 6 provides a non-limiting illustration of such placement. For example, the mobile communication device 600 may comprise a main body portion 620 and an audio output portion 610 (e.g., an earpiece). A first electrode may be disposed on the main body portion 620 (e.g., molded into the main body portion 620 or positioned on the main body portion 620). A second electrode may be disposed on the audio output portion 610 (e.g., molded into the audio output portion 610 or positioned on the audio output portion 610). Such electrode placement may, for example, provide for user contact with both electrodes during the process of listening to the MCD 100.

Though the previous exemplary illustrations generally discuss one or two electrodes, it should be recognized that more than two electrodes might also be utilized. For example, the MCD 100 may be adapted to detect cardiac activity of a user that is conductively coupled to at least two of a first, second and third (or N) electrodes.

In general, one or more electrodes may be disposed in any of a variety of locations on the MCD 100 and related components (e.g., peripheral components). Accordingly, the scope of various aspects of the present invention should not be limited by characteristics of any particular electrode placement.

Figure 7:
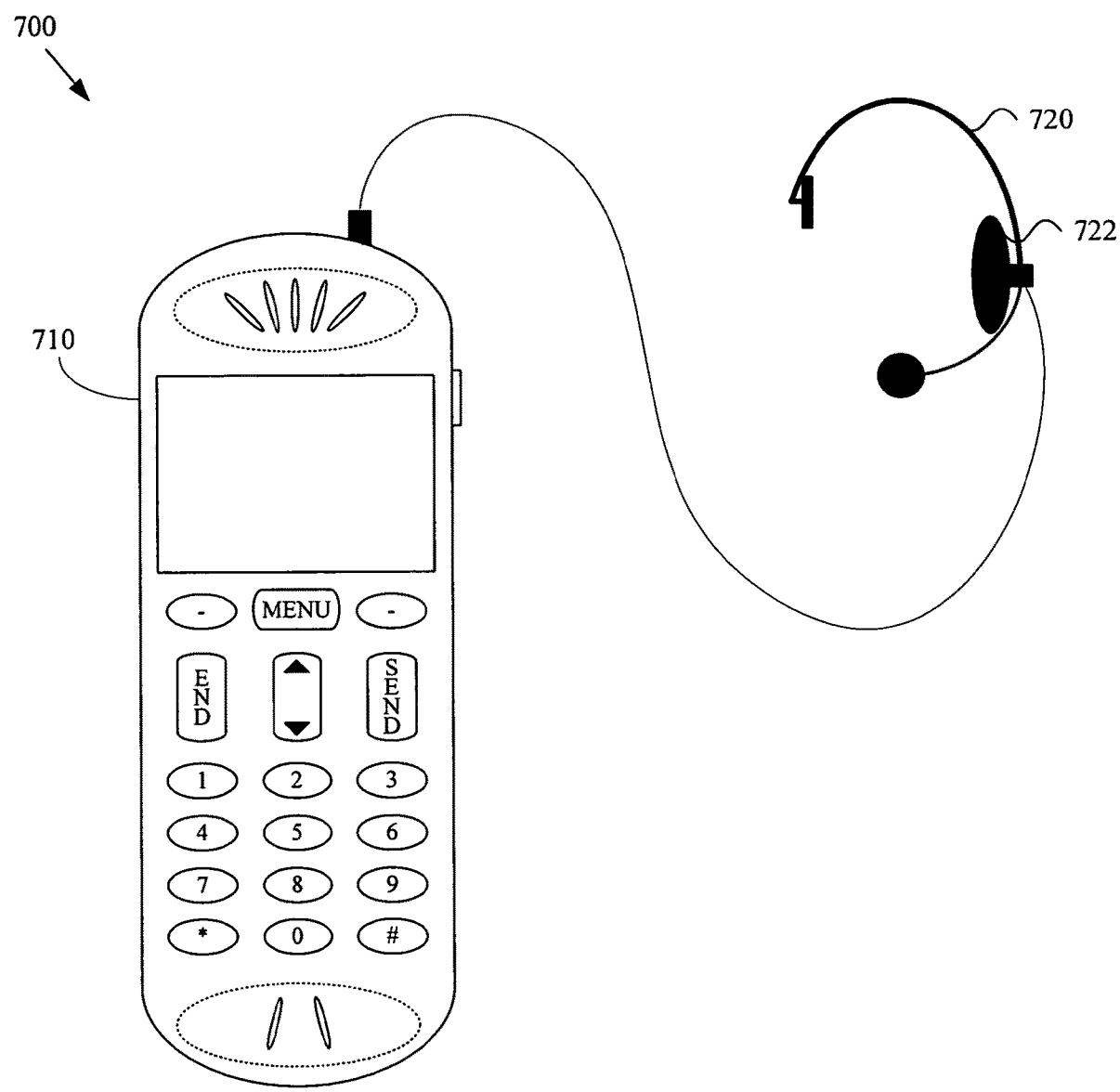
FIG. 7 is a diagram illustrating an exemplary mobile communication device, in accordance with various aspects of the present invention.

As illustrated in FIG. 7, a mobile communication device 700 may comprise a main body portion 710 and a second portion 720 that is separate from the main body portion 710. For example and without limitation, such a second portion 720 may comprise characteristics of a headset, earphone, microphone or other hands-free mechanism (or adapter). In the non-limiting exemplary illustration in FIG. 7, the second portion 720 may comprise an earpiece comprising an electrode 722 (or other sensor). In such an exemplary configuration, an electrode need not necessarily be placed on or near the main portion 710 of the mobile communication device 700.

Figure 8:
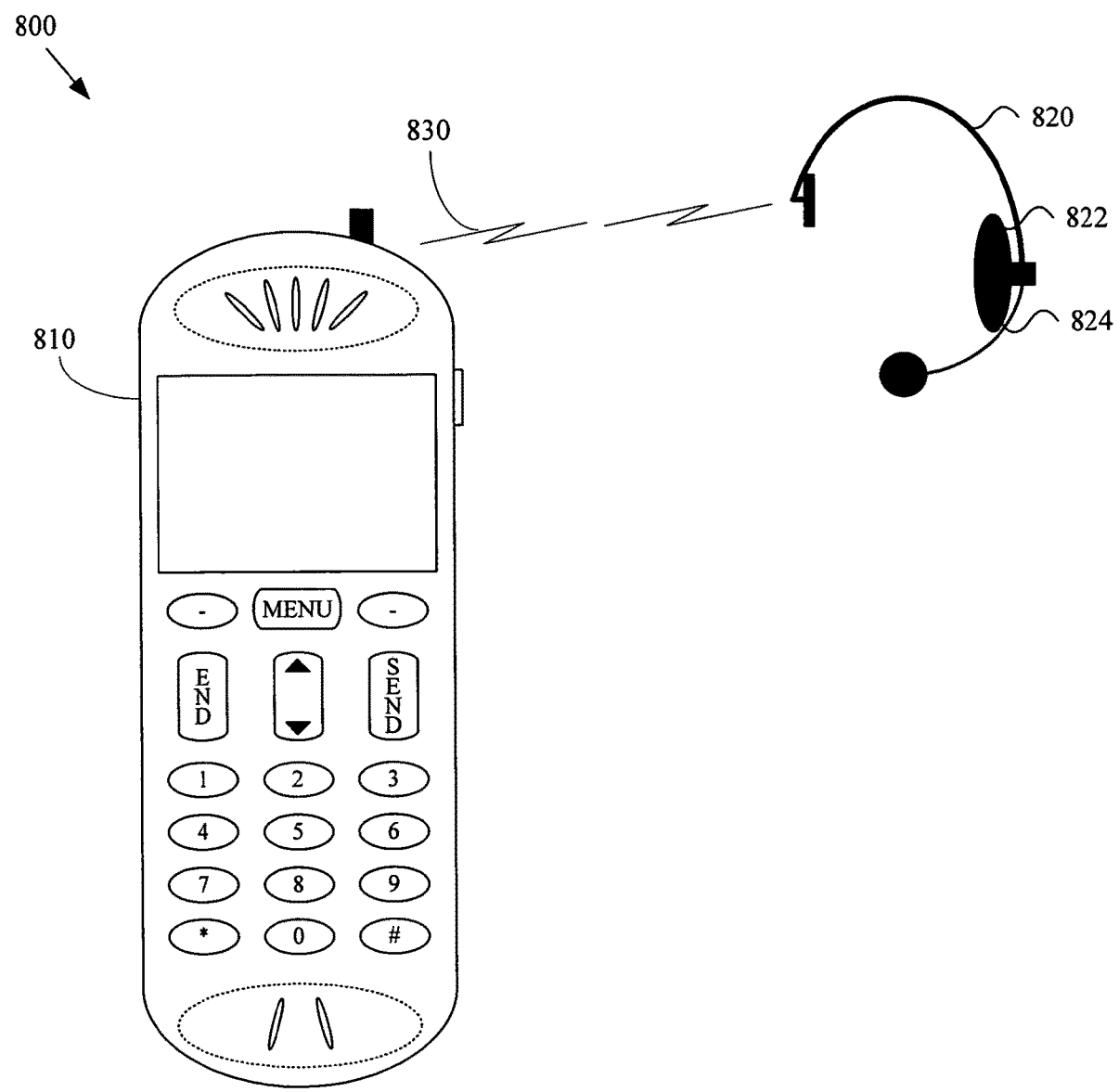
FIG. 8 is a diagram illustrating an exemplary mobile communication device, in accordance with various aspects of the present invention.

As illustrated in FIG. 8, a mobile communication device 800 may comprise a main body portion 810 and a second portion 820 that is separate from the main body portion 810. For example and without limitation, such a second portion 820 may comprise characteristics of a headset, earphone, microphone or other hands-free mechanism (or adapter). In the non-limiting exemplary illustration in FIG. 8, the second portion 820 may comprise at least a first electrode 822 and a second electrode 824 (or other sensor arrangement), information from which may be wirelessly communicated to the main body portion 810.

Figure 9:
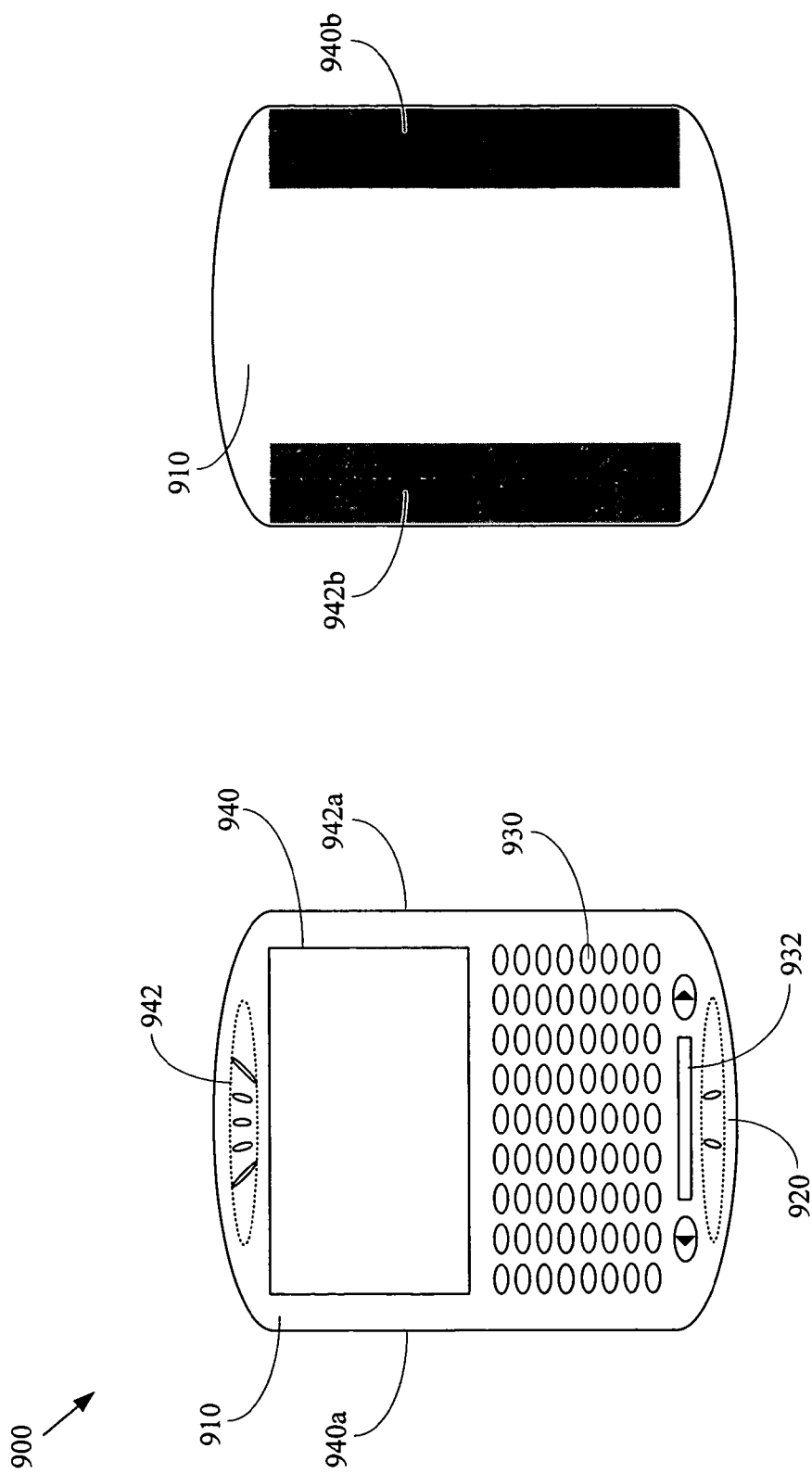
FIG. 9 is a diagram illustrating an exemplary mobile communication device, in accordance with various aspects of the present invention.

As mentioned previously, a mobile communication device may comprise characteristics of any of a variety of mobile communication devices. Though the previous illustrations were generally directed to an illustrative mobile telephone, the scope of various aspects of the present invention should by no means be limited by characteristics of a mobile telephone. For example and without limitation, FIG. 9 is a diagram illustrating an exemplary mobile communication device 900 in accordance with various aspects of the present invention. The exemplary mobile communication device

900 may generally comprise characteristics of a portable email device or personal digital assistant.

The exemplary mobile communication device 900 may, for example and without limitation, share various characteristics with the exemplary mobile communication devices (or portions thereof) illustrated in FIGS. 1-8 and discussed previously. For example, the exemplary mobile communication device 900 may comprise a main body portion 910, an audio input portion 920, various pushbuttons (e.g., a space bar 932 and alphanumeric button 930, an output display 940, an audio output portion 942, etc.). The exemplary mobile communication device 900 may also comprise a left side portion 940 and right side portion 942. Analogous to the previously discussed mobile communication devices, the exemplary mobile communication device 900 may comprise one or more electrodes on any of a variety of components and in any of a variety of locations.

In another non-limiting exemplary scenario, a mobile communication device may be utilized in an automobile environment. For example and without limitation, an automobile may comprise a mobile communication device permanently, pseudo-permanently or temporarily located in the automobile. In such a scenario, one or more cardiac sensors may be positioned in locations within the automobile (e.g., in one or more positions in which a user may readily contact such sensors). For example and without limitation, one or more cardiac sensors (e.g., electrodes) may be disposed on a steering wheel, shifting lever or other commonly contacted automobile component. In one example, a first cardiac sensing electrode may be disposed on a left side of a steering wheel, and a second cardiac sensing electrode may be disposed on a right side of a steering wheel. In such an exemplary configuration, each of the left and right hands may advantageously contact respective cardiac sensors for extended periods of time and also during stressful situations. Also, in such an exemplary configuration, sensor information may, for example, be communicated (as exemplified in FIGS. 7 and 8) to the mobile communication device by wire or wirelessly.

Figure 10:
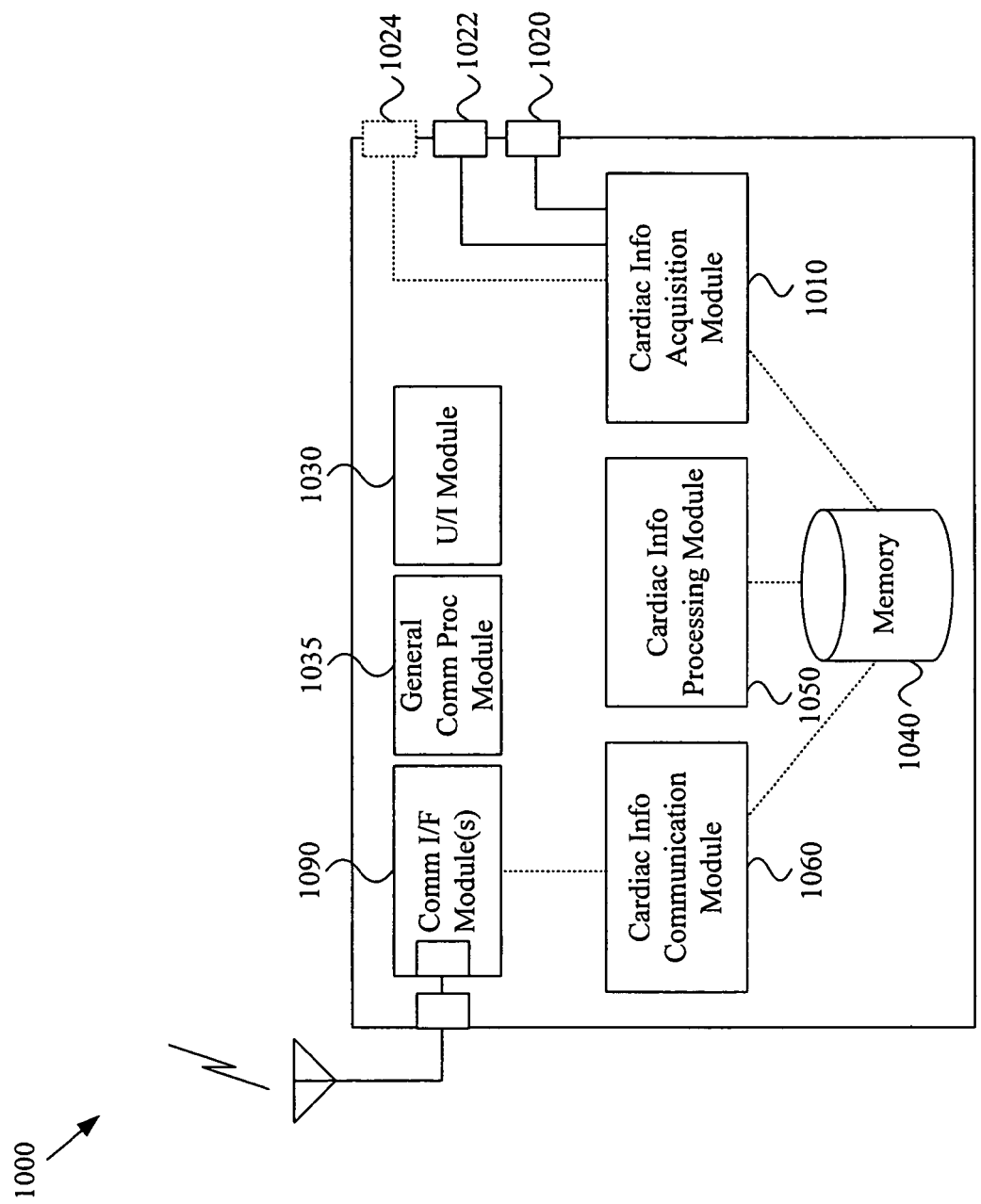
FIG. 10 is a block diagram illustrating portions of an exemplary mobile communication device, in accordance with various aspects of the present invention.

FIG. 10 is a block diagram illustrating an exemplary mobile communication device 1000 ("MCD") (or portions thereof) in accordance with various aspects of the present invention. Various exemplary modules will be addressed in more detail later. The exemplary MCD 1000 may, for example, comprise a first electrode 1020 and a second electrode 1022 (and, for example, a third or Nth electrode 1024). Alternatively for example, the exemplary MCD 1000 may comprise any of a variety of sensors (e.g., audio sensors) for monitoring cardiac activity. The exemplary MCD 1000 may also comprise a cardiac information acquisition module 1010 that is coupled to the first and second electrodes 1020, 1022 and utilizes the first and second electrodes 1020, 1022 to detect and acquire various cardiac (i.e., heart-related) signals from a user.

The cardiac information acquisition module 1010 may then, for example, store acquired cardiac information in a memory 1040. As will be explained later, the mobile communication device 1000 may also comprise a cardiac information processing module 1050 that processes acquired cardiac information and a cardiac information communication module 1060 that communicates acquired cardiac information or analysis results to another system. The exemplary mobile communication device 1000 is also illustrated with various general communication components, including a U/I module 1030, general communication processing module 135 and communication interface module(s) 1090.

Summarizing portions of the previous discussion, various aspects of the present invention provide a mobile communication device (and other electronic devices) with cardiovascular monitoring capability.

Figure 11:
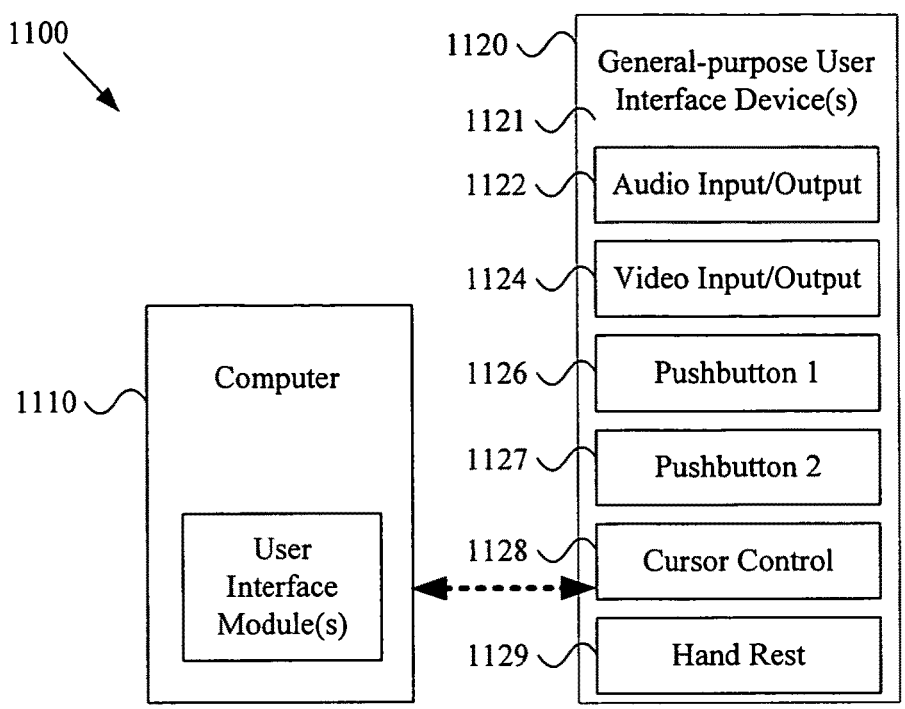
FIG. 11 is a diagram illustrating portions of an exemplary computer system and/or user interface device, in accordance with various aspects of the present invention.

FIG. 11 is a diagram illustrating an exemplary computer system 1100, including a computer 1110 and an exemplary general-purpose user interface device 1120, in accordance with various aspects of the present invention. The exemplary general-purpose user interface device 1120 may, for example and without limitation, share various characteristics with the exemplary mobile communication devices, and portions thereof, illustrated in FIGS. 1-10 and discussed previously. The following discussion will generally refer to FIG. 11, with occasional reference to FIGS. 12-15.

The computer system 1110 may comprise characteristics of any of a variety of computer system types. For example and without limitation, the computer system 1110 may comprise characteristics of a desktop computer, laptop or notebook computer, handheld computer, mainframe computer, etc.

The general-purpose computer user interface device 1120 may generally be considered to be a computer user interface device like that typically utilized in general interaction with a computer. In other words, the general-purpose computer user interface device 1120 is not dedicated to the acquisition of cardiac information. For example and without limitation, as illustrated in FIGS. 12-15, the user interface device 1120 may comprise characteristics of a keyboard or keypad, mouse, cursor control device, video I/O device, audio I/O device, gaming controller, or other computer user interface devices that are used during the course of general (or typical) user interaction with a computer.

The exemplary user interface device 1120 is illustrated with a non-limiting exemplary set of user interface components (or modules). For example, the user interface device 1120 may comprise a main body portion 1121 (e.g., a primary casing or housing for the user interface device).

The user interface device 1120 may also comprise one or more audio input/output devices 1122. Such devices may, for example and without limitation, comprise speakers, earphones, headsets, microphones, etc. The user interface device 1120 may also comprise one or more video input/output devices 1124. Such devices may, for example and without limitation, comprise video displays, CRTs, LCD displays, plasma displays, touch screen displays, etc.

The user interface device 1120 may also comprise one or more pushbuttons (e.g., the first pushbutton 1126 and second pushbutton 1127). Such pushbuttons may comprise any of a variety of characteristics, some of which were discussed previously with regard to the pushbuttons of the mobile communication device (or portions thereof) illustrated in FIGS. 1-10. The pushbuttons may, for example and without limitation, comprise keyboard or keypad keys, mouse buttons, volume controllers, scroll controllers, selection buttons, up/down or left/right arrows, etc.

The user interface device 1120 may also comprise one or more cursor control features 1128. Such cursor control features 1128 may, for example and without limitation, comprise characteristics of a touch pad, mouse pad, eraser head controller, trackball, thumb wheel, etc. The user interface device 1120 may also comprise one or more hand rest portions 1129. For example and without limitation, such hand rest portions 1129 may comprise palm or wrist contact points on a keyboard, a palm-resting place on a mouse, etc.

Various user interface features were discussed previously. Any one, combination of, or all of such user interface features may comprise one or more cardiac sensors (e.g., an electrode, plurality of electrodes, audio input device, etc.) that are adapted to detect cardiac activity of a user of the user interface device 1120. For example, such electrodes may be adapted to detect cardiac activity of user that is conductively coupled to electrodes (e.g., by touching the electrodes). Various electrode characteristics were discussed previously with regard to the mobile communication device (and portions thereof) illustrated in FIGS. 1-10. For the sake of brevity, only a portion of the previous discussion will be repeated here. It should be noted that various electrode characteristics discussed previously (e.g., electrode formation, placement, shape, size, integration, identification, numbers, features, etc.) apply to the user interface devices discussed herein as well as the mobile communication device(s) discussed previously.

For example, an electrode (or other sensor) may be disposed on a first pushbutton 1126 or second pushbutton 1127 of the user interface device 1120. Also for example, an electrode may be disposed on a hand rest 1129, hand-held portion and/or main body portion 1121 of the user interface device 1120. Additionally for example, an electrode may be disposed on a side portion of the user interface device 1120 or on a portion of the user interface device 1120 that is separate from the main body portion 1121. Further for example, an electrode may be disposed on a cursor control component 1128 of the user interface device 1120 (e.g., a touch pad, eraser-head cursor control feature, thumb wheel, trackball, active mouse pad, etc.). Still further for example, an electrode may be disposed on a volume control feature (e.g., of an audio input/output device 1122) or on a touch screen (or other portion) of a video input/output device 1124.

In general, one or more electrodes (or other sensors) may be disposed on the user interface device 1120 such that the electrodes contact a user during normal use of the user interface device. Such normal use may, for example and without limitation, comprise typing on a keyboard or keypad, listening to a headset, typing or entering information with pushbuttons, controlling a cursor, interacting with a monitor, utilizing a mouse, utilizing a game controller to play a video game, etc.

First and second (or more) electrodes (or other sensors) may be disposed in various positions relative to the user interface device 1120 and each other. For example and without limitation, a first electrode may be disposed on the main body portion 1121 of the user interface device 1120, and a second electrode may also be disposed on the main body portion 1121 of the user interface device 1120. Also for example, a first electrode may be disposed on the main body portion 1121 of the user interface device 1120, and a second electrode may be disposed on a pushbutton 1126 of the user interface device 1120. Further for example, a first electrode and second electrode may both be disposed on the first pushbutton 1126. Still further for example, a first electrode may be disposed on the first pushbutton 1126, and a second electrode may be disposed on the second pushbutton 1127. In another example, first and/or second electrodes may be disposed on a feature of the general-purpose computer user interface device 1120 that is dedicated to detecting cardiac activity.

The previously discussed electrode placements are merely exemplary, and the scope of various aspects of the present invention should not be limited by characteristics of any particular electrode placement.

The following discussion will present various non-limiting exemplary general-purpose computer user interface devices. The purpose of such presentation is to provide specific illustrations of generally broader aspects of the present invention. Accordingly, the scope of various aspects of the present invention should not be limited by characteristics of the exemplary illustrations.

Figure 12:
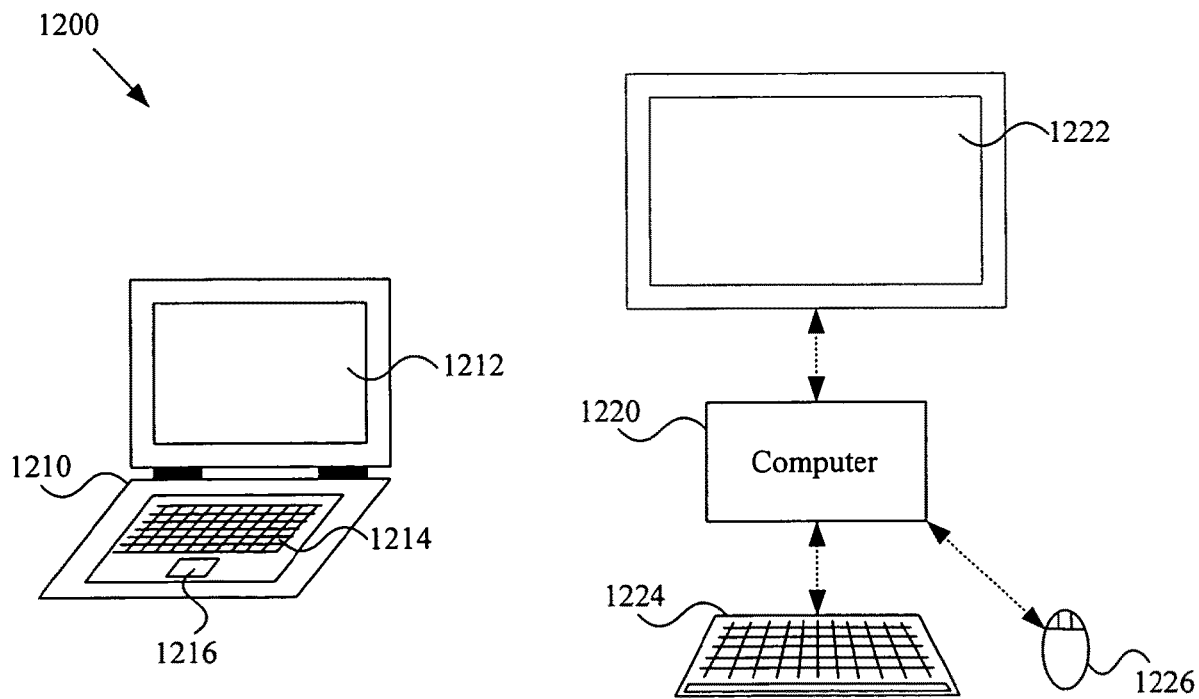
FIG. 12 is a diagram illustrating exemplary general-purpose computer user interface devices, in accordance with various aspects of the present invention.

FIG. 12 is a diagram illustrating exemplary general-purpose computer user interface devices 1200, in accordance with various aspects of the present invention. An exemplary desktop computer system 1220 comprises a display device 1222, which may, for example, comprise a touch screen. The desktop computer system 1220 also comprises a keyboard 1224 and a mouse 1226. The display device 1222, keyboard 1224 and mouse 1226 are all examples of general-purpose computer user interface devices. The exemplary laptop computer system 1210 comprises a display 1212 (which may comprise touch screen capability), a keyboard 1214 and a touch pad 1216 for cursor control. The display 1212, keyboard 1214 and touch pad 1216 are all examples of general-purpose computer user interface devices.

As with the various exemplary mobile communication devices (and portions thereof) illustrated in FIGS. 1-10 and discussed previously, though the following computer user interface device examples will generally refer to cardiac sensing electrodes, the scope of various aspects of the present invention readily extend to other cardiac sensing devices (e.g., audio monitoring or acoustical sensing devices).

Figure 13:
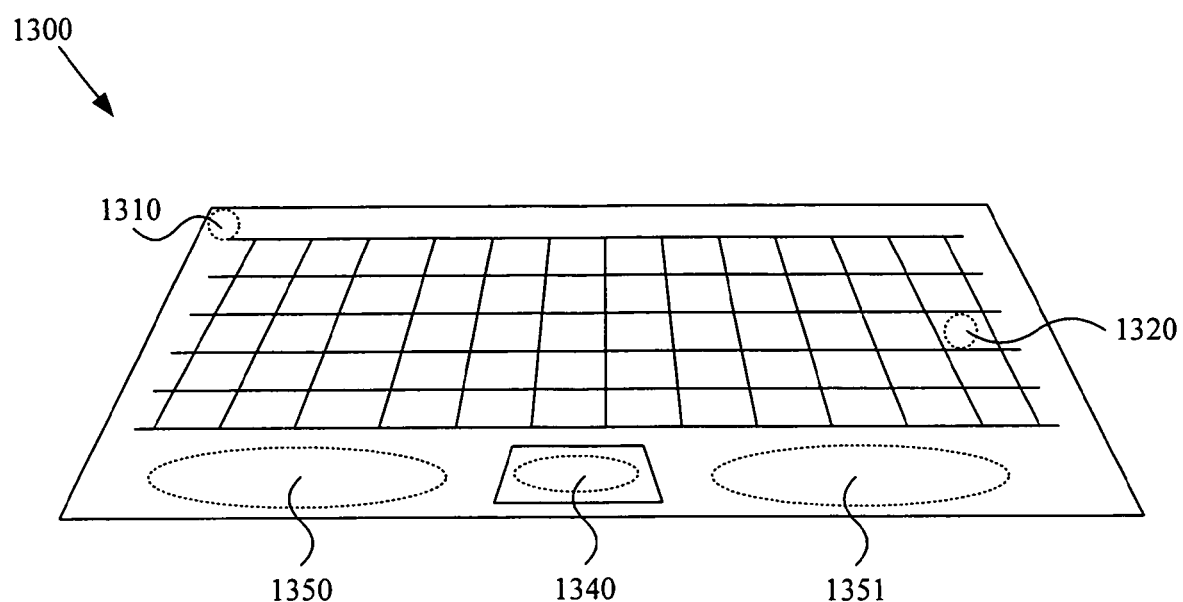
FIG. 13 is a diagram illustrating an exemplary general-purpose computer keyboard, in accordance with various aspects of the present invention.

FIG. 13 is a diagram illustrating an exemplary general-purpose computer keyboard 1300, in accordance with various aspects of the present invention. The exemplary keyboard 1300 may, for example, comprise one or more cardiac sensors 1310 (e.g. electrodes and/or acoustic sensors) on a main body portion. The keyboard 1300 may, for example, comprise an electrode on a first hand rest 1350 and/or an electrode on a second hand rest 1351. The keyboard 1300 may also comprise an electrode 1340 disposed on a touch pad, and one or more electrodes 1320 disposed on a pushbutton (e.g., a key) of the keyboard 1300.

Figure 14:
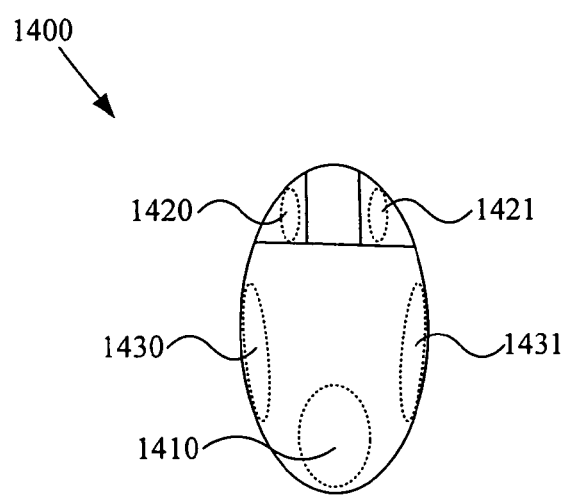
FIG. 14 is a diagram illustrating an exemplary general-purpose computer mouse, in accordance with various aspects of the present invention.

FIG. 14 is a diagram illustrating an exemplary general-purpose computer mouse 1400, in accordance with various aspects of the present invention. The exemplary mouse 1400 may, for example, comprise an electrode 1410 on a central main body portion of the mouse 1400. Also for example, the mouse 1400 may comprise an electrode 1430 on a first side of the mouse 1400 and/or an electrode 1431 on a second side of the mouse 1400. Further for example, the mouse 1400 may comprise one or more electrodes 1420 on a left-click pushbutton of the mouse 1400 and/or one or more electrodes 1421 on a right-click pushbutton of the mouse 1400.

Figure 15:
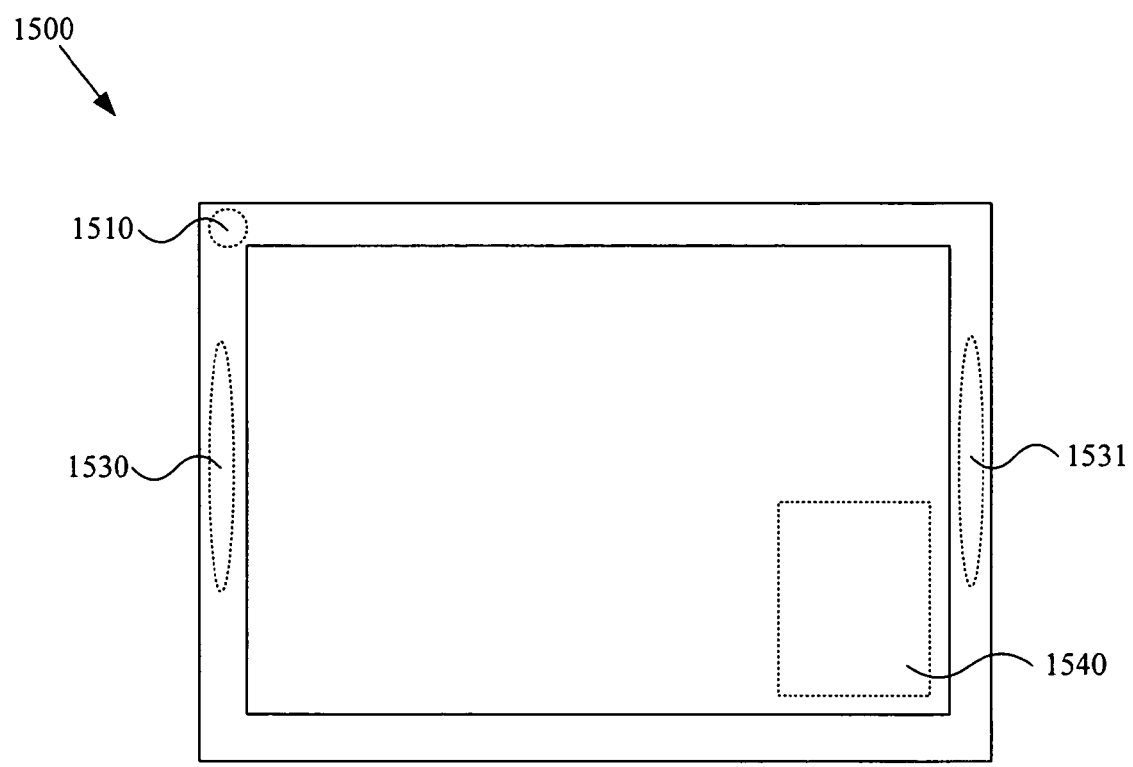
FIG. 15 is a diagram illustrating an exemplary video display device, in accordance with various aspects of the present invention.

FIG. 15 is a diagram illustrating an exemplary computer display device 1500, in accordance with various aspects of the present invention. The display device 1500 may, for example, comprise an electrode 1510 on a border portion of the display device 1500. Also for example, the display device 1500 may comprise an electrode 1530 on a first side of the display device 1500 and/or an electrode 1531 on a second side of the display device 1500. Further for example, the display device 1500 may comprise one or more electrodes 1540 on a touch screen portion of the display device 1500.

Though not illustrated here, as discussed previously with regard to the mobile communication devices (or portions thereof) illustrated in FIGS. 1-10, the user interface device may also comprise characteristics of a headset (e.g., including a speaker and/or microphone) or earpiece. Also for example, though not necessarily considered to be "general-purpose," various aspects of the present invention may be extended to various computer attachments, such as, for example, gaming controllers and various peripherals.

It should be recognized that various aspects of the present invention may also be applied to other electronic devices. For example, as mentioned previously, various gaming controllers (e.g., joysticks, consoles, firearm simulators, pads, pushbuttons, etc.) may comprise cardiac sensors disposed on commonly contacted components, which would enable the collection of cardiac information from a user of such devices. In such a non-limiting exemplary scenario, cardiac information obtained from such sensors may be utilized for health purposes and other purposes. For example and without limitation, information from various sensors (e.g., electrodes or acoustical sensors) disposed on a gaming control may be utilized to control operation of the video game. For example, information obtained from various sensors may reflect stress level, anxiety, relaxation, etc. A video game may then, for example, utilize such information to modify characteristics of a game to achieve a particular emotional or physical goal.

Figure 16:
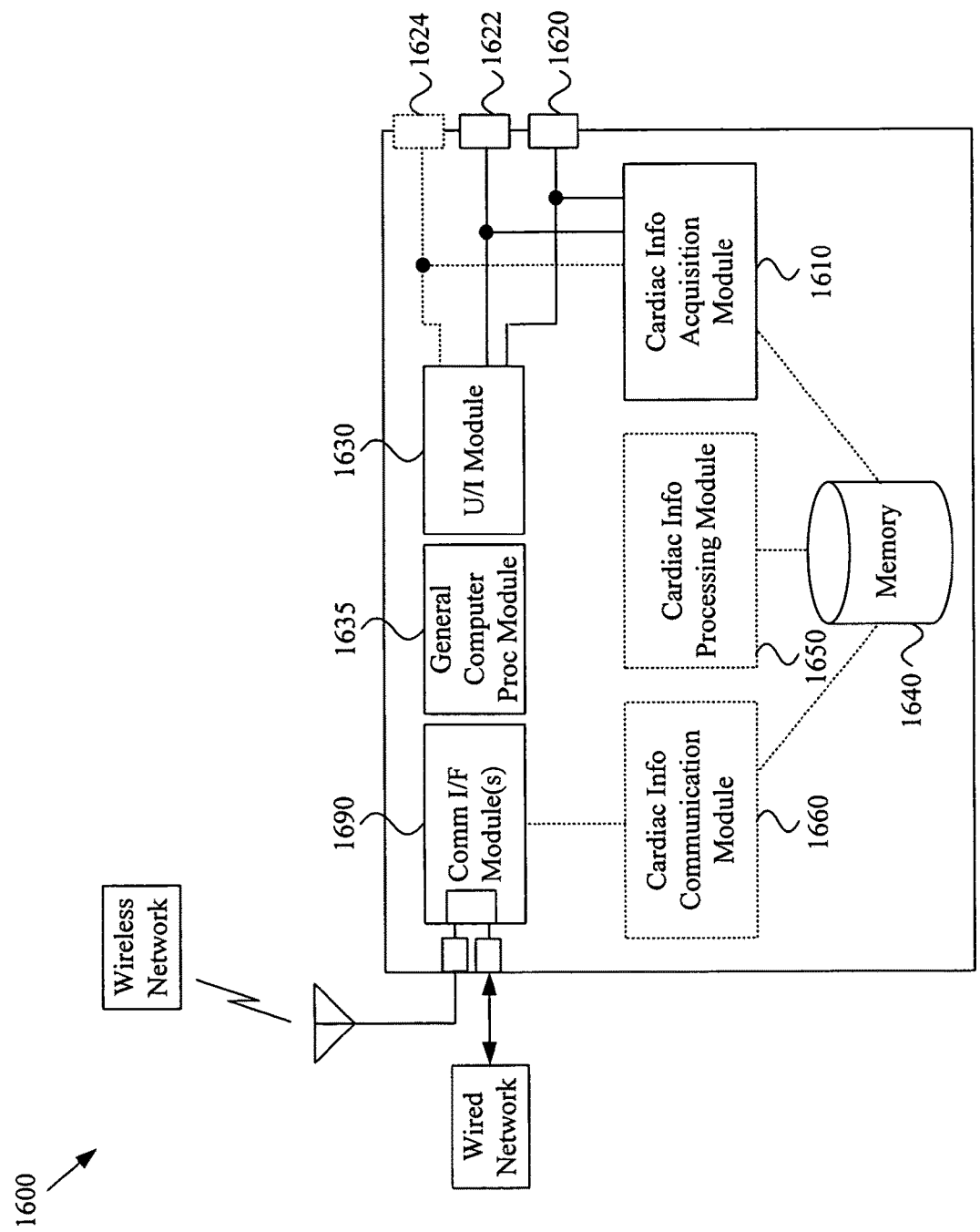
FIG. 16 is a block diagram illustrating exemplary computer and/or general-purpose computer user interface device modules, in accordance with various aspects of the present invention.

FIG. 16 is a block diagram illustrating an exemplary computer system 1600, in accordance with various aspects of the present invention. The exemplary modules of the computer system 1600 are merely illustrative and should by no means limit the scope of various aspects of the present invention.

The exemplary computer system 1600 may, for example, comprise a first U/I device port 1620 (for coupling to a first U/I device comprising at least one cardiac electrode or other sensor) and a second U/I port 1622 (for coupling to a second U/I device comprising at least one cardiac electrode or other sensor). The exemplary computer system 1600 may also comprise a third U/I port 1624 or any number of U/I ports (some or all of which may be adapted to couple various modules to various user interface devices having one or more cardiac electrodes). The exemplary computer system 1600 may also comprise a cardiac information acquisition module 1610 that is coupled to the first and second U/I ports 1620, 1622 and which utilizes various electrodes (or other sensors) of a first and/or second U/I interface device coupled to the first and/or second U/I ports 1620, 1622 to detect and acquire various cardiac signals from a user. Note that one or more user interface modules 1630 may also be coupled to the U/I ports 1620, 1622, and 1624.

The cardiac information acquisition module 1610 may then, for example, store acquired cardiac information in a memory 1640. As will be explained later, the exemplary computer system 1600 may also comprise a cardiac information processing module 1650 that processes acquired cardiac information and a cardiac information communication module 1660 that communicates acquired cardiac information or analysis results to another system (e.g., through a communication interface module 1690, either wired, tethered or wireless).

Summarizing portions of the previous discussion, various aspects of the present invention provide a general-purpose computer user interface device with cardiovascular monitoring capability.

Figure 17:
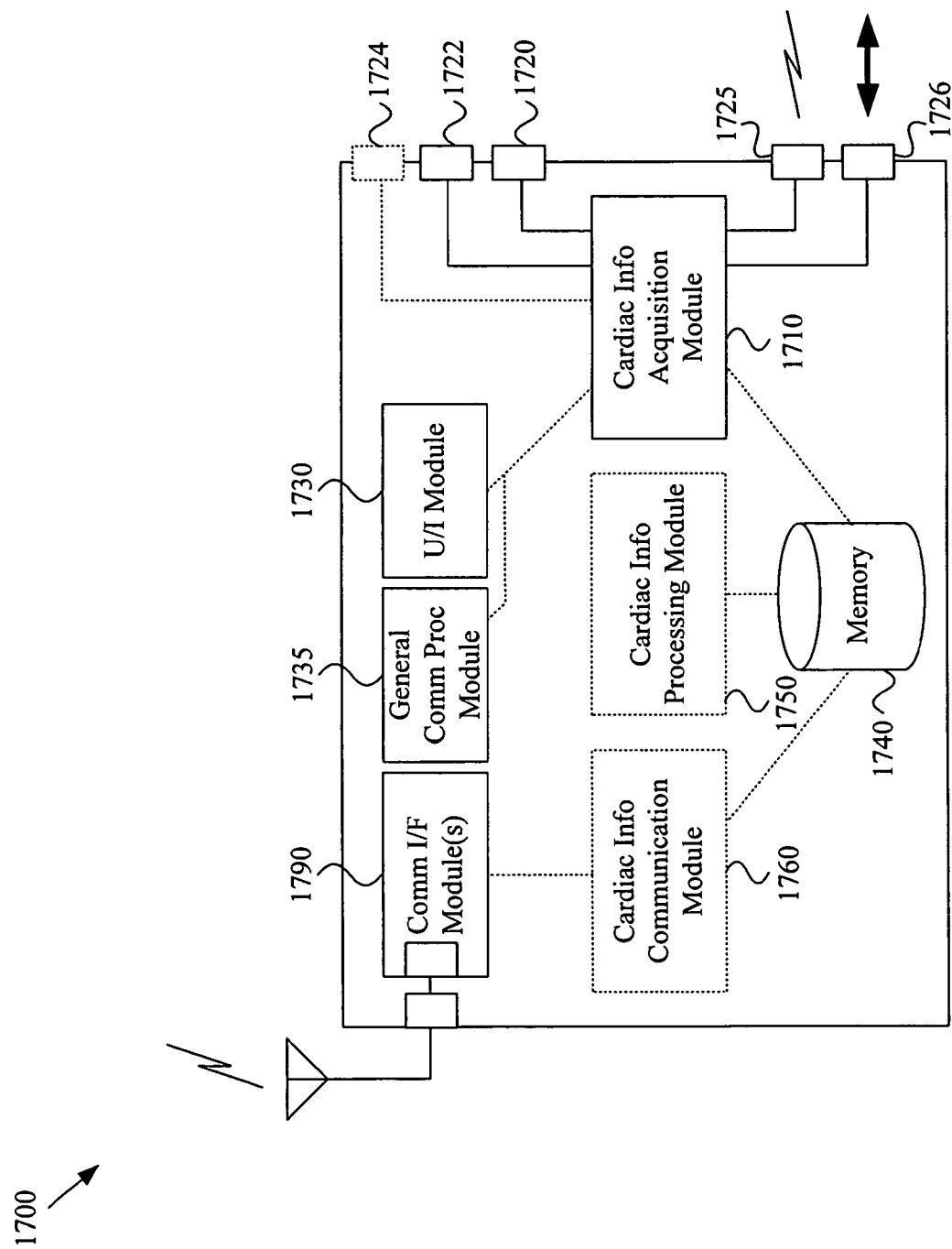
FIG. 17 is a block diagram illustrating various portions of an exemplary mobile communication device, in accordance with various aspects of the present invention.

FIG. 17 is a block diagram illustrating various portions of an exemplary mobile communication device 1700, in accordance with various aspects of the present invention. The exemplary mobile communication device 1700 may, for example and without limitation, share various characteristics with the mobile communication devices, and other exemplary devices, illustrated in FIGS. 1-16 and discussed previously.

The exemplary mobile communication device 1700 ("MCD") may comprise characteristics of any of a variety of mobile communication devices, some of which were discussed previously. For example and without limitation, the MCD 1700 may comprise characteristics of a portable phone, cellular phone, portable email device, portable computer with mobile communication capability, paging device, etc.

The exemplary MCD 1700 may be adapted to acquire cardiac information from a user of the mobile communication device 1700. The exemplary MCD 1700 may, for example, comprise a communication interface module 1790 (e.g., a general-purpose communication interface module). The communication interface module 1790 may, for example, be adapted to perform communications between the mobile communication device 1700 and one or more general communication networks. The exemplary MCD 1700 may also comprise a general communication processing module 1735 that is generally adapted to support general communication between the MCD 1700 and one or more communication networks, and a user interface module 1730 that is generally adapted to provide a user interface between a user of the MCD 1700 and the MCD 1700.

The exemplary MCD 1700 may also comprise a cardiac information acquisition module 1710 that is adapted to acquire cardiac information from a user of the MCD 1700. In a first non-limiting exemplary scenario, the cardiac information acquisition module 1710 may be adapted to interface with a cardiac sensor (e.g., electrodes or an acoustical sensor). Such a cardiac sensor may, for example, be disposed on the MCD 1700. As a non-limiting example, the exemplary MCD 1700 may comprise a first electrode 1720 and a second electrode 1722 (e.g., and a third electrode 1724 or Nth electrode) disposed on the MCD 1700 (e.g., in a manner conducive to making contact with a user during normal use of the MCD 1700). Various exemplary characteristics of such a cardiac sensor or electrodes were discussed previously.

As another non-limiting example, the exemplary MCD 1700 may comprise various cardiac sensor communication ports (e.g., the first cardiac sensor communication port 1725 and the second cardiac sensor communication port 1726), which may, for example, be adapted to communicate with cardiac sensing components and/or circuits and systems separate from, and communicatively coupled to, the MCD 1700. Such external cardiac sensing components may, for example, be disposed on various devices coupled to the MCD 1700 (e.g., user I/O components, hands-free components, etc.), some of which were discussed previously. In various non-limiting exemplary scenarios, such an external cardiac sensing component may also comprise characteristics of cardiac sensing devices disposed within the user's body (e.g., independently or combined with a pacemaker or defibrillator).

The cardiac information acquisition module 1710 may, for example, be adapted to communicate with any of a variety of cardiac sensing components and/or systems (e.g., through the cardiac sensor communication ports 1725, 1726). Such communication may, for example, be governed by standard and/or proprietary communication protocols. Non-limiting examples of such communication protocols may comprise Bluetooth, IEEE 802.11, UWB, IEEE 802.15, Zigbee, etc. Further for example, such communication may be governed, at least in part, by a propriety protocol that is customized for the communication of cardiac information. In general, the cardiac information acquisition module 1710 may utilize various communication ports (e.g., the first cardiac sensor communication port 1725 and second cardiac sensor communication port 1726) to receive cardiac information over any of a variety of communication networks (e.g., LANs, PANs, WANs, the Internet, etc.).

The cardiac information acquisition module 1710 may, for example, be adapted to acquire cardiac information from a user of the MCD 1700 continually or in response to any of a variety of causes and conditions. For example and without limitation, the cardiac information acquisition module 1710 may be adapted to detect user interaction with a cardiac sensor, and acquire cardiac information in response to, at least in part, detecting user interaction with a cardiac sensor. For example, such user interaction may comprise a user of the MCD 1700 conductively contacting one or more cardiac monitoring electrodes.

Also for example, the cardiac information acquisition module 1710 may be adapted to detect an incoming communication (e.g., through a cardiac sensor communication port) regarding cardiac information, and acquire cardiac information in response to, at least in part, detecting such an incoming communication. Further for example, the cardiac information acquisition module 1710 may be adapted to detect use of the MCD 1700 by a user, and acquire cardiac information in response to, at least in part, detecting such use. The cardiac information acquisition module 1710 may, for example, be adapted to interface with the user interface module 1730 and/or the general communication processing module 1735 to determine when the MCD 1700 is being utilized by the user.

The cardiac information acquisition module 1710 may, for example, be adapted to periodically attempt to acquire cardiac information from a user or may be adapted to continually attempt to acquire such information. The cardiac information acquisition module 1710 may also, for example, be adapted to acquire cardiac information from a user governed by acquisition constraints or directives included in a profile (e.g., stored in the memory 1740). Such a profile may, for example, include information-directing behavior of the cardiac information acquisition module 1710 (e.g., timing behavior, triggering behavior, sensor interface behavior, UI behavior, etc.).

The cardiac information acquisition module 1710 may, for example, be adapted to acquire cardiac information from a user of the MCD 1700 in response to a user command (e.g., as received through the user interface module 1730). Additionally, for example, the cardiac information acquisition module 1710 may be adapted to acquire cardiac information from a user of the MCD 1700 in response to a command or request received from another communication system (e.g., through the communication interface module 1790 and/or the general communication processing module 1735).

The cardiac information acquisition module 1710 may, for example, be adapted to acquire cardiac information from the user in any of a variety of manners. For example, the module 1710 may be adapted to utilize the user interface module 1730 to communicate with the user before, during and/or after the acquisition process. For example, the cardiac information acquisition module 1710 may utilize the user interface module 1730 to instruct the user about a procedure to follow or to provide results of cardiac information acquisition to the user.

In acquiring cardiac information, the cardiac information acquisition module 1710 may, for example, interact with one or more cardiac sensors (e.g., cardiac electrodes). Such interaction may, for example, comprise transmitting and/or receiving digital or analog signals. Such interaction may, for example, comprise digitally sampling received analog signals prior to digital storage, processing and/or communication. Such interaction may, for example, be generally governed by the nature (e.g., active or passive nature) of a particular cardiac sensor.

The cardiac information acquisition module 1710 may also, for example, be adapted to identify the user of the MCD 1700. For example, such identification (or authentication) may be utilized in an exemplary scenario where a variety of users may be utilizing the MCD 1700. In such an exemplary scenario, the acquisition module 1710 may be adapted to acquire cardiac information for a plurality of different users and to segment such information according to user identity.

After the acquisition of user cardiac information, the MCD 1700 may perform various additional activities, some of which will be discussed later. For example and without limitation, the MCD 1700 may store, analyze and/or communicate acquired cardiac information. For example, the cardiac information acquisition module 1710 may store acquired cardiac information (or a portion thereof) in the memory 1740. Other modules of the MCD 1700 may then access such stored information from the memory 1740. Such memory 1740 may, for example, comprise characteristics of volatile or non-volatile memory (e.g., so that cardiac information may be saved between powered-up sessions of the MCD 1700). In a non-limiting exemplary scenario where the cardiac information acquisition module 1710 acquires cardiac information from a plurality of users, the acquisition module 1710 may store at least a portion of such acquired information in the memory 1740 (e.g., indexed by user identification).

The previous exemplary mobile communication device 1700 illustration was presented to provide specific illustrations of various generally broader aspects of the present invention. Various aspects of the present invention may also be applied to other electronic devices. For example and without limitation, a general-purpose computer may be adapted to be communicatively coupled to a general-purpose computer user interface device (e.g., as discussed previously) and comprise at least one module adapted to interface with such a general-purpose computer user interface device to acquire user cardiac information.

Figure 18:
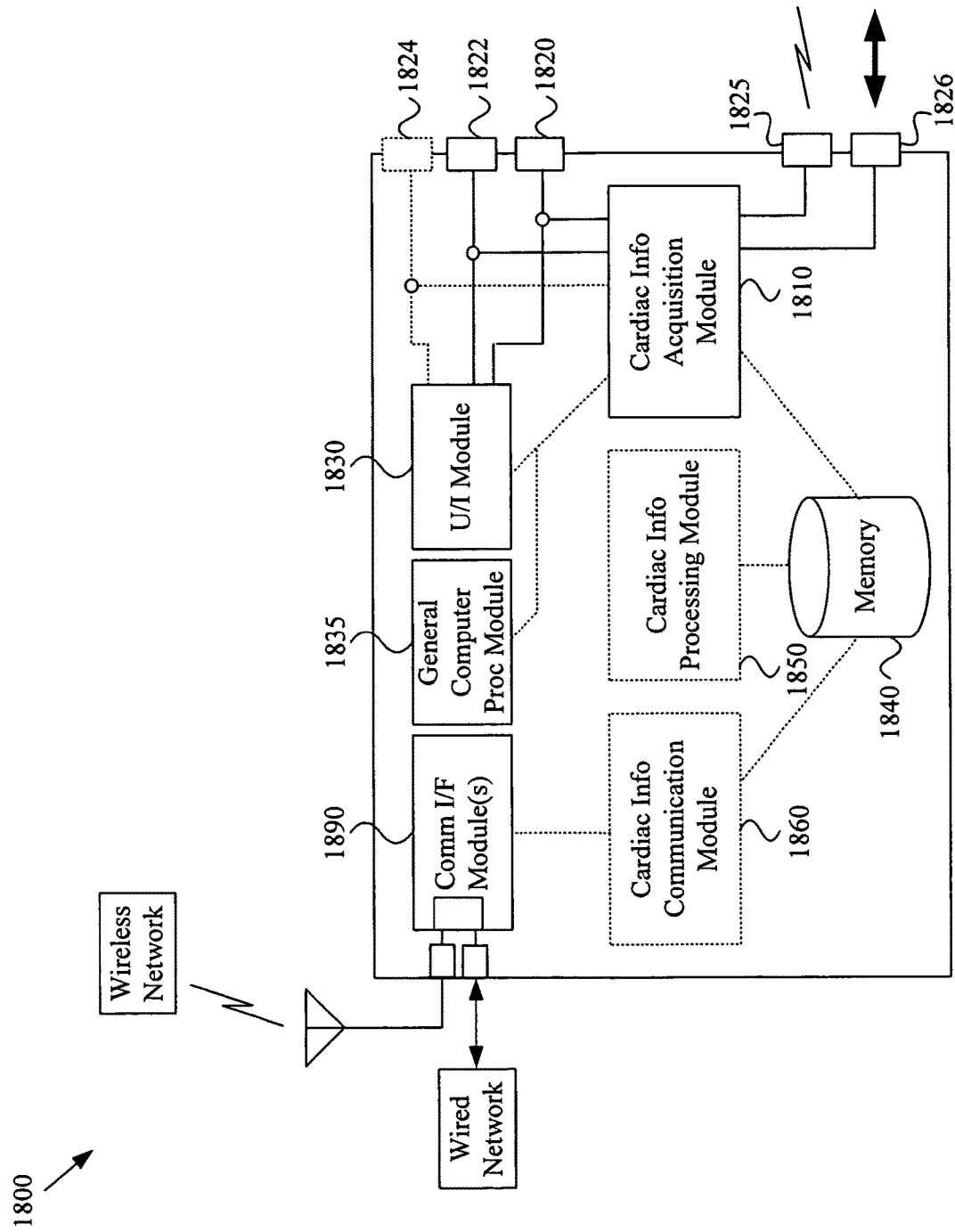
FIG. 18 is a block diagram illustrating various portions of an exemplary computer system, in accordance with various aspects of the present invention.

FIG. 18 is a block diagram illustrating various portions of an exemplary computer system 1800, in accordance with various aspects of the present invention. The exemplary computer system 1800 may, for example and without limitation, share various characteristics with the exemplary computer system 1600 illustrated in FIG. 16 and discussed previously.

The exemplary computer system 1800 may, for example, comprise a first U/I device port 1820 (for coupling to a first U/I device comprising at least one cardiac sensor or electrode) and a second U/I device port 1822 (for coupling to a second U/I device comprising at least one cardiac sensor or electrode). The exemplary computer system 1800 may also comprise a third U/I device port 1824 or any number of U/I device ports (some or all of which may be adapted to couple various modules to various user interface devices having one or more cardiac sensors).

Similar to the exemplary mobile communication device 1700 of FIG. 17, the exemplary computer system 1800 may comprise one or more cardiac information communication ports (e.g., the first cardiac communication port 1825 and the second cardiac communication port 1826).

Similar to the exemplary mobile communication device 1700 of FIG. 17, the exemplary computer system 1800 may also comprise a cardiac information acquisition module 1810 that may be coupled to the first and second U/I ports

1820, 1822 and which utilizes various sensors or electrodes of a first and/or second U/I interface device coupled to the first and/or second U/I ports 1820, 1822 to detect and acquire various cardiac signals from a user. The exemplary cardiac information acquisition module 1810 may also, for example, be coupled to the first and second cardiac communication ports 1825, 1826 and adapted to receive cardiac information from various sensing devices transmitting such information. In general, the exemplary cardiac information acquisition module 1810 may share various characteristics with the cardiac information acquisition module 1710 of the exemplary mobile communication device 1700 illustrated in FIG. 17 and discussed previously.

Figure 19:
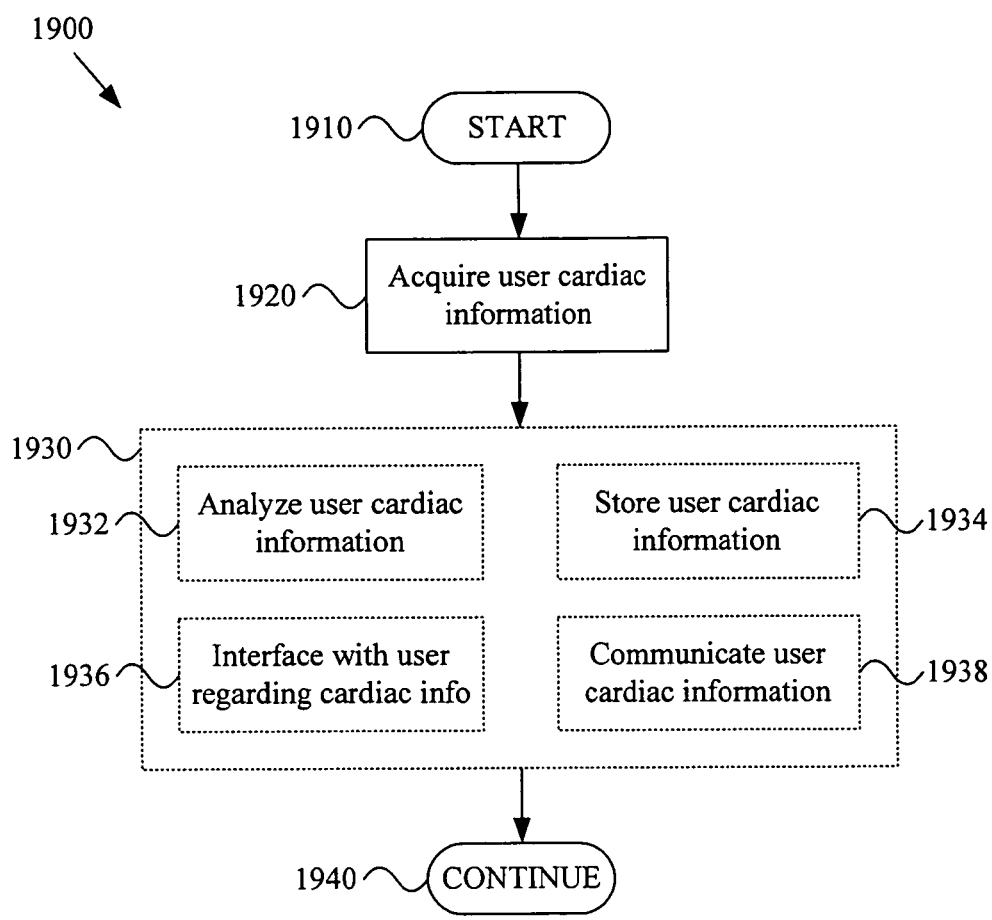
FIG. 19 is a flow diagram illustrating an exemplary method, in a mobile communication device or other device, for acquiring cardiac information of a user, in accordance with various aspects of the present invention.

FIG. 19 is a block diagram illustrating an exemplary method 1900, in a mobile communication device (or other device), for acquiring cardiac information of a user, in accordance with various aspects of the present invention. The exemplary method 1900 may, for example and without limitation, share various functional characteristics with the exemplary mobile communication device 1700 and computer system 1800 illustrated in FIGS. 17-18 and discussed previously.

The exemplary method 1900 may begin executing at step 1910 for any of variety of reasons, some of which were discussed previously with regard to the MCD 1700 of FIG. 17. The exemplary method 1900 may, at step 1920, comprise acquiring user cardiac information (e.g., from a user of a mobile communication device or general-purpose computer user interface device). Such acquisition was generally discussed previously with regard to the MCD 1700 of FIG. 17 (e.g., the cardiac information acquisition module 1710 and various related modules).

The exemplary method 1900 may, at step 1930, comprise performing various additional functions related to the cardiac information acquired at step 1920. For example and without limitation, step 1932 may comprise analyzing at least a portion of acquired cardiac information. Various characteristics of such analysis will be discussed later. Also for example, step 1934 may comprise storing at least a portion of acquired cardiac information in a memory. Non-limiting examples of storage were discussed previously with regard to the cardiac information acquisition module 1710 and memory 1740 of the exemplary MCD of FIG. 17. Further for example, step 1936 may comprise interfacing with a user regarding the acquired cardiac information. Non-limiting examples of such user interaction were discussed previously with regard to the cardiac information acquisition module 1710 and the U/I module 1730 of the exemplary MCD of FIG. 17. Still further for example, step 1938 may comprise communicating acquired user cardiac information with other communication systems. Various characteristics of such communication will be discussed later.

The exemplary method 1900 may, at step 1940, comprise performing any of a variety of continued processing. Such continued processing may, for example, comprise acquiring, communicating and/or analyzing additional cardiac information. Various non-limiting examples of such continued processing were presented previously and will also be presented later.

Figure 20:
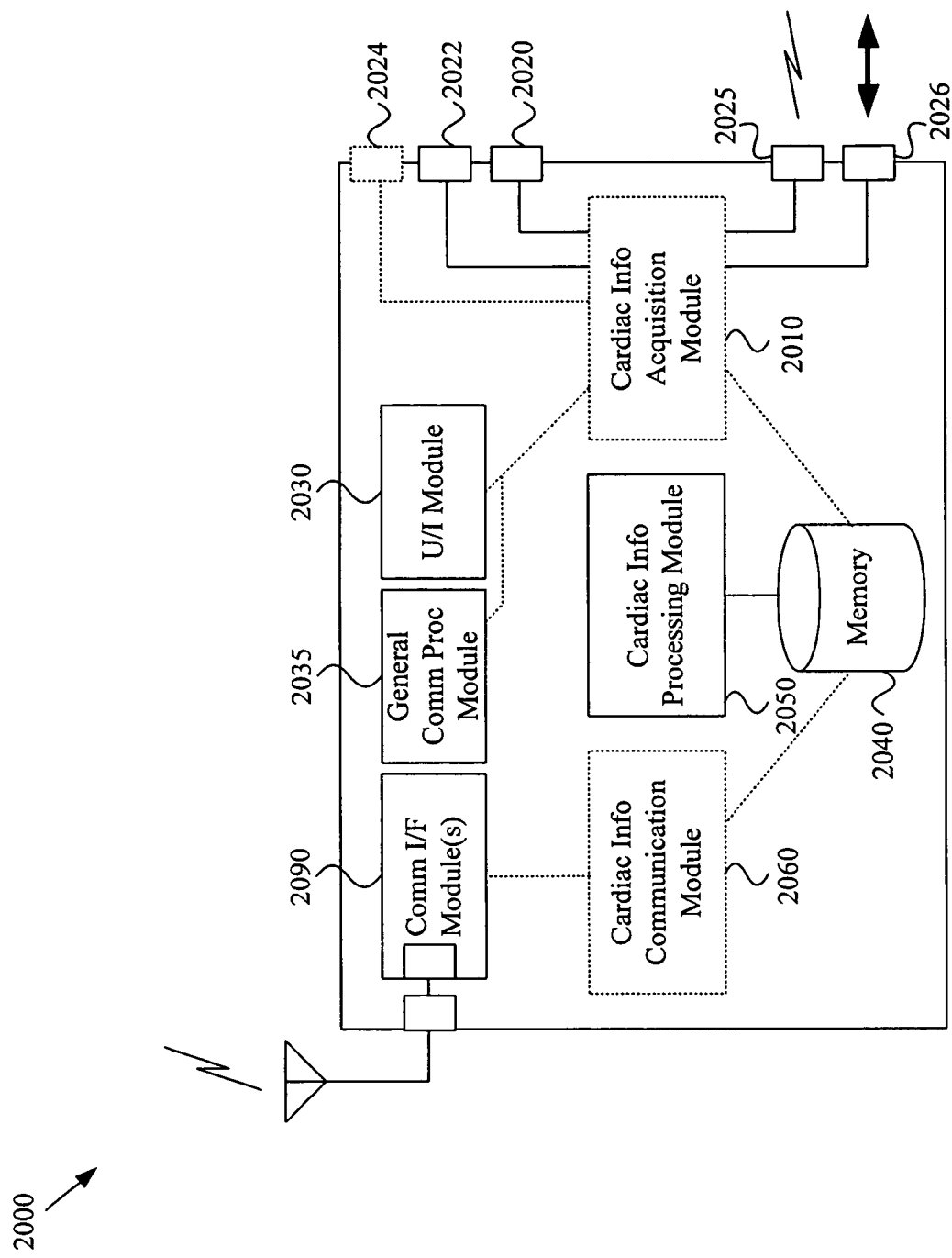
FIG. 20 is a block diagram illustrating various portions of an exemplary mobile communication device, in accordance with various aspects of the present invention.

FIG. 20 is a block diagram illustrating various portions of an exemplary mobile communication device 2000, in accordance with various aspects of the present invention. The exemplary mobile communication device 2000 may, for example and without limitation, share various characteristics with the exemplary mobile communication devices and other devices illustrated in FIGS. 1-19 and discussed previously. For example, the mobile communication device 2000 may comprise characteristics of any of a variety of mobile communication devices.

The exemplary mobile communication device 2000 may comprise a communication interface module 2090 that is adapted to communicate with one or more general-purpose communication networks. The communication interface module 2090 may, for example and without limitation, share various characteristics with previously discussed communication interface modules (e.g., the communication interface module 1790 of the exemplary mobile communication device 1700 illustrated in FIG. 17). The exemplary mobile communication device 2000 may also comprise a general communication processing module 2035 and a user interface module 2030, which may, for example, share various characteristics with analogous modules discussed previously.

The exemplary mobile communication device 2000 may also, for example and without limitation, comprise a cardiac information acquisition module 2010, various cardiac sensors (e.g., electrodes) 2020, 2022, 2024 and various cardiac information communication ports 2025, 2026. As discussed previously with regard to other exemplary communication devices, such modules or components may, for example, be utilized to acquire cardiac information (e.g., from a user of the mobile communication device 2000. Such modules and/or components are merely one illustration of a manner in which cardiac information may be acquired for analysis by the exemplary mobile communication device 2000.

The exemplary mobile communication device 2000 may additionally, for example, comprise a cardiac information-processing module 2050 (or analysis module). The processing module 2050 may process (e.g., analyze) cardiac information in any of a variety of manners. The following discussion will present various non-limiting examples of such processing. Note that in various exemplary scenarios, the cardiac information processed by the processing module 2050 might be stored in the memory 2040.

The following discussion will generally provide non-limiting illustrations of processing cardiac information in light of various cardiac pathologies. Such pathologies may, for example and without limitation, comprise various ischemic diseases, acute coronary syndrome (ischemic chest pain), acute myocardial infarction (heart attacks), arrhythmias tachyarrhythmias (fast rate disturbances), bradyarrhythmias (slow rate disturbances), etc. Although the following discussion generally provides illustrations of processing cardiac information in light of such pathologies, the scope of various aspects of the present invention should not be limited by characteristics of particular pathologies or pathologies in general. For example, various aspects of the present invention may apply equally to non-pathology cardiac areas. For example and without limitation, various aspects of the present invention may also apply to cardiac information related to general health monitoring, fetus monitoring, medication effectiveness monitoring, etc.

Cardiac signals may, for example, comprise a primary component (e.g., frequency component) and a variety of residual components (or harmonic components). The processing module 2050 may, for example, be adapted to analyze cardiac information by, at least in part, analyzing a primary component of a cardiac signal. For example, the processing module 2050 may be adapted to analyze the cardiac information by, at least in part, comparing a primary component characteristic of the cardiac signal to one or more primary component characteristics associated with a known cardiac pathology. Such a primary component characteristic may, without limitation, comprise frequency, signal level, signal shape or statistical characteristics (e.g., medium value, mean value, variance, standard deviation, etc.).

The processing module 2050 may, for example, be adapted to process current cardiac information and previous cardiac information (e.g., generally corresponding to a first cardiac signal and at least a second cardiac signal). For example and without limitation, the processing module 2050 may be adapted to analyze cardiac information by determining a difference between a current cardiac signal (e.g., a primary component thereof) and at least one previous cardiac signal (e.g., a primary component thereof) and determining the existence of a cardiac pathology based, at least in part, on the determined difference. For example, the processing module 2050 may be adapted to determine the existence of a cardiac pathology by comparing the determined difference to at least one difference characteristic associated with a known cardiac pathology.

In a non-limiting exemplary scenario, the processing module 2050 may be adapted to compare changes in a cardiac signal to known pathologic patterns (e.g., ST-segment depression or ST-segment elevation). As mentioned previously, analysis of cardiac signal (or information) changes over time may comprise analyzing changes in heart rate or other heart characteristics (e.g., to monitor effectiveness of anti-arrhythmic medication, blood pressure medication or other medication).

The processing module 2050 may, for example, be adapted to process current and previous cardiac information corresponding to any of a variety of time intervals. For example and without limitation, the processing module 2050 may be adapted to determine short-term or long-term differences in a cardiac signal and to analyze such short-term or long-term differences.

The processing module 2050 may also, for example, be adapted to process more than two cardiac signals. For example and without limitation, the processing module 2050 may be adapted to analyze cardiac information by determining a trend between a current cardiac signal (e.g., a primary component thereof) and at least two previous cardiac signals (e.g., respective primary components thereof) and determining the existence of a cardiac pathology based, at least in part, on the determined trend. For example, the processing module 2050 may be adapted to determine the existence of a cardiac pathology by comparing the determined trend to at least one trend characteristic associated with a known cardiac pathology.

The processing module 2050 may also, for example, be adapted to analyze cardiac information by, at least part, analyzing one or more residual (or harmonic) components of a cardiac signal. For example, the processing module 2050 may be adapted to compare one or more residual component characteristics of the cardiac signal to one or more residual component characteristics associated with a known cardiac pathology. Such residual characteristics may, without limitation, comprise frequency, signal level, signal shape or statistical characteristics (e.g., median value, mean value, variance, standard deviation, etc.).

As mentioned previously, the processing module 2050 may, for example, be adapted to process current cardiac information and previous cardiac information (e.g., generally corresponding to a first cardiac signal and at least a second cardiac signal). For example and without limitation, the processing module 2050 may be adapted to analyze cardiac information by determining a difference between a current cardiac signal (e.g., at least one residual component thereof) and at least one previous cardiac signal (e.g., at least one residual component thereof) and determining the existence of a cardiac pathology based, at least in part, on the determined difference. For example, the processing module 2050 may be adapted to determine the existence of a cardiac pathology by comparing the determined difference to at least one difference characteristic associated with a known cardiac pathology.

Also as mentioned previously, the processing module 2050 may, for example, be adapted to process more than two cardiac signals. For example and without limitation, the processing module 2050 may be adapted to analyze cardiac information by determining a trend between a current cardiac signal (e.g., at least one residual component thereof) and at least two previous cardiac signals (e.g., respective residual components thereof) and determining the existence of a cardiac pathology based, at least in part, on the determined trend. For example, the processing module 2050 may be adapted to determine the existence of a cardiac pathology by comparing the determined trend to at least one trend characteristic associated with a known cardiac pathology.

The processing module 2050 may, for example, be adapted to perform spectral analysis of various cardiac signals (or signals derived therefrom). For example and without limitation, the processing module 2050 may be adapted to perform spectral analysis on a cardiac signal by, at least in part, comparing the frequency spectrum of the cardiac signal (e.g., a primary component or residual components thereof) with a frequency spectrum associated with a known cardiac pathology. Further for example, the processing module 2050 may be adapted to determine a difference (or trend) between a current cardiac signal at least one previous cardiac signal, and determine the existence of a cardiac pathology based, at least in part, on spectral analysis of the determined difference (or trend).

As mentioned previously, various types of cardiac information may be obtained using audio monitoring or acoustical sensing (or detecting) devices. The processing module 2050 may, for example and without limitation, process such information to determine various cardiovascular characteristics. For example and without limitation, such characteristics may comprise characteristics relating to blood pressure, contractility, blood flow and turbulence, etc. As discussed previously, cardiac information may be acquired from any of a variety of sources. Such information (e.g., digital and/or analog signals) may be analyzed (e.g., by the processing module 2050) to determine any of a large variety of cardiac conditions. Accordingly, the scope of various analysis aspects of the present invention should not be limited by characteristics of cardiac information obtained from any particular source (e.g., an electrode source, audio monitoring source, etc.).

The previous analysis examples are merely exemplary, and accordingly, the scope of various aspects of the present invention should not be limited by characteristics of particular types of cardiac information processing.

In various non-limiting exemplary scenarios, the mobile communication device 2000 (e.g., the processing module 2050) may be adapted to generate (or initiate generation of) an alert message based, at least in part, on the cardiac information analysis. For example and without limitation, the alert message may comprise characteristics of an alert message directed to the user of the mobile communication device 2000. The processing module 2050 may, for example, utilize the user interface module 2030 to generate an output notification to the user. Also for example, the alert message may comprise characteristics of a notification communicated to a second communication system. The processing module 2050 may, for example, utilize the communication interface module 2090 and/or the general communication-processing module 2035 to communicate such a notification. The alert message may, for example, be communicated to any of a variety of destinations (e.g., a health care facility, a physician, an emergency care facility, an ambulance service, 911 service, police and fire departments, etc.).

The previous exemplary mobile communication device 2000 was presented to provide specific illustrations of various generally broader aspects of the present invention. Various aspects of the present invention may also be applied to other electronic devices. For example and without limitation, a general-purpose computer may be adapted to process cardiac information.

Figure 21:
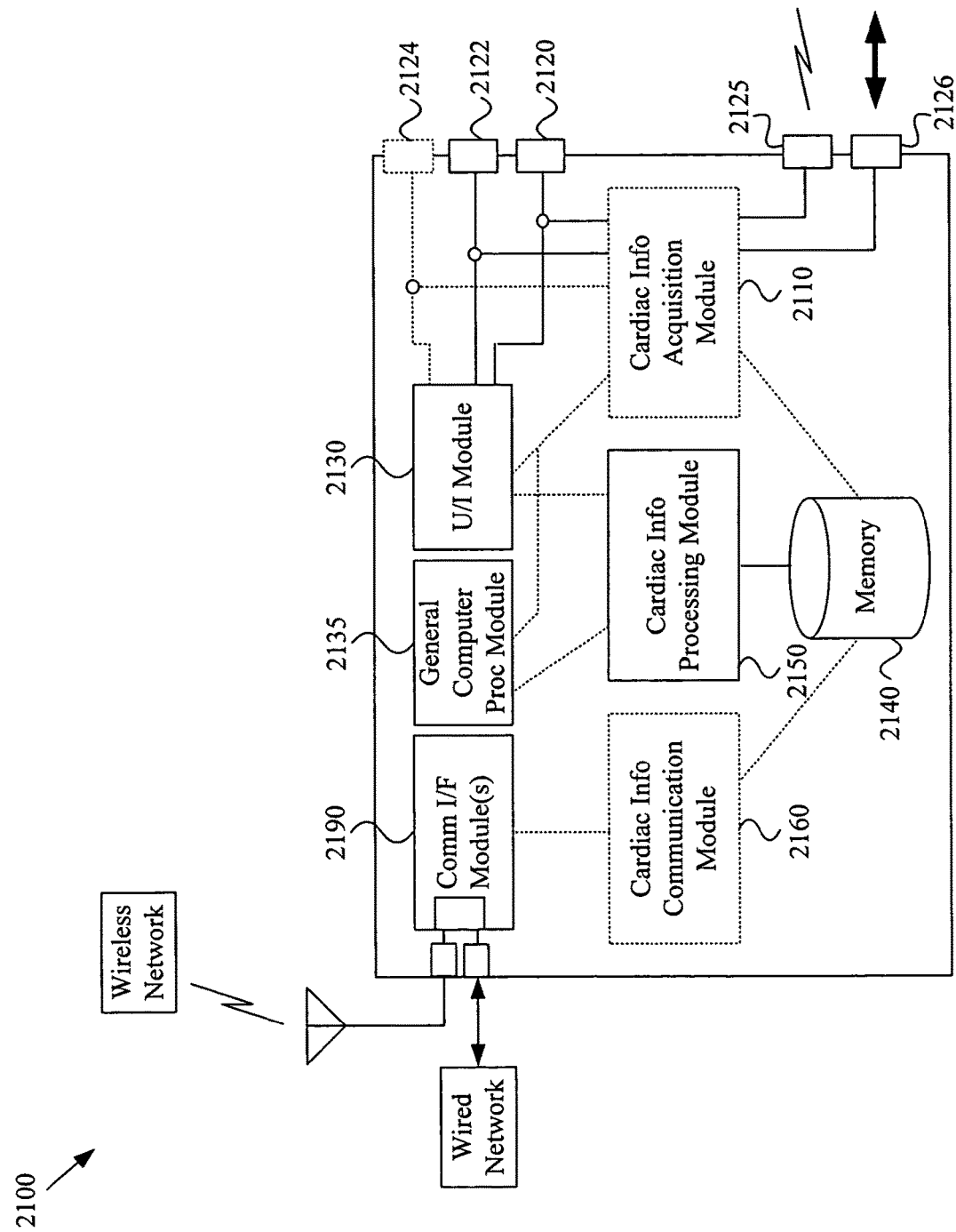
FIG. 21 is a block diagram illustrating various portions of an exemplary computer system, in accordance with various aspects of the present invention.

FIG. 21 is a block diagram illustrating various portions of an exemplary computer system 2100, in accordance with various aspects of the present invention. The exemplary computer system 2100 may, for example and without limitation, share various characteristics with the exemplary computer system 1800 illustrated in FIG. 18 and discussed previously. The exemplary computer system 2100 may, for example, comprise various interfaces to a general-purpose computer user interface device (various examples of which were presented previously). Such interfaces may, for example and without limitation, comprise a source of cardiac information, which may be analyzed by the cardiac information-processing module 2150.

The following discussion will generally be directed to the cardiac information-processing module 2150 of the exemplary computer system 2100. The cardiac information processing module 2150 of the exemplary computer system 2100 may, for example and without limitation, share various characteristics with the cardiac information processing module 2050 of the mobile communication system 2000 illustrated in FIG. 20 and discussed previously. The processing module 2150 may, for example, be adapted to analyze cardiac information obtained from a user of the computer system 2100 (e.g., acquired by the cardiac information acquisition module 2110).

As discussed previously with regard to the mobile communication device 2000 illustrated in FIG. 20, the processing module 2150 may, for example, be adapted to analyze cardiac information by, at least in part, analyzing a primary component of a cardiac signal. For example, the processing module 2150 may be adapted to analyze the cardiac information by comparing at least one primary component characteristic of a cardiac signal to one or more primary component characteristics associated with a known cardiac pathology.

Also as discussed previously with regard to the mobile communication device 2000 illustrated in FIG. 20, the processing module 2150 may, for example, be adapted to analyze cardiac information by, at least in part, analyzing a residual component of a cardiac signal or plurality of such signals. For example, the processing module 2150 may be adapted to analyze the cardiac information by comparing at least one residual component characteristic of a cardiac signal (or plurality of such signals) to one or more residual component characteristics associated with a known cardiac pathology.

Additionally as discussed previously with regard to the mobile communication device 2000 illustrated in FIG. 20, the processing module 2150 may, for example, be adapted to analyze cardiac information by, at least in part, performing spectral analysis on a cardiac signal. Also for example, the processing module 2150 may be adapted to perform such spectral analysis with a plurality of signals. For example and without limitation, the processing module 2150 may be adapted to analyze the cardiac information by determining a difference between a current cardiac signal at least one previous cardiac signal, and determining the existence of a cardiac pathology based, at least in part, on spectral analysis of the determined difference.

Still further as discussed previously, the computer system 2100 (e.g., the processing module 2150 and various other modules of the computer system) may be adapted to generate an alert message based, at least in part, on cardiac information analysis performed by the processing module 2150.

Figure 22:
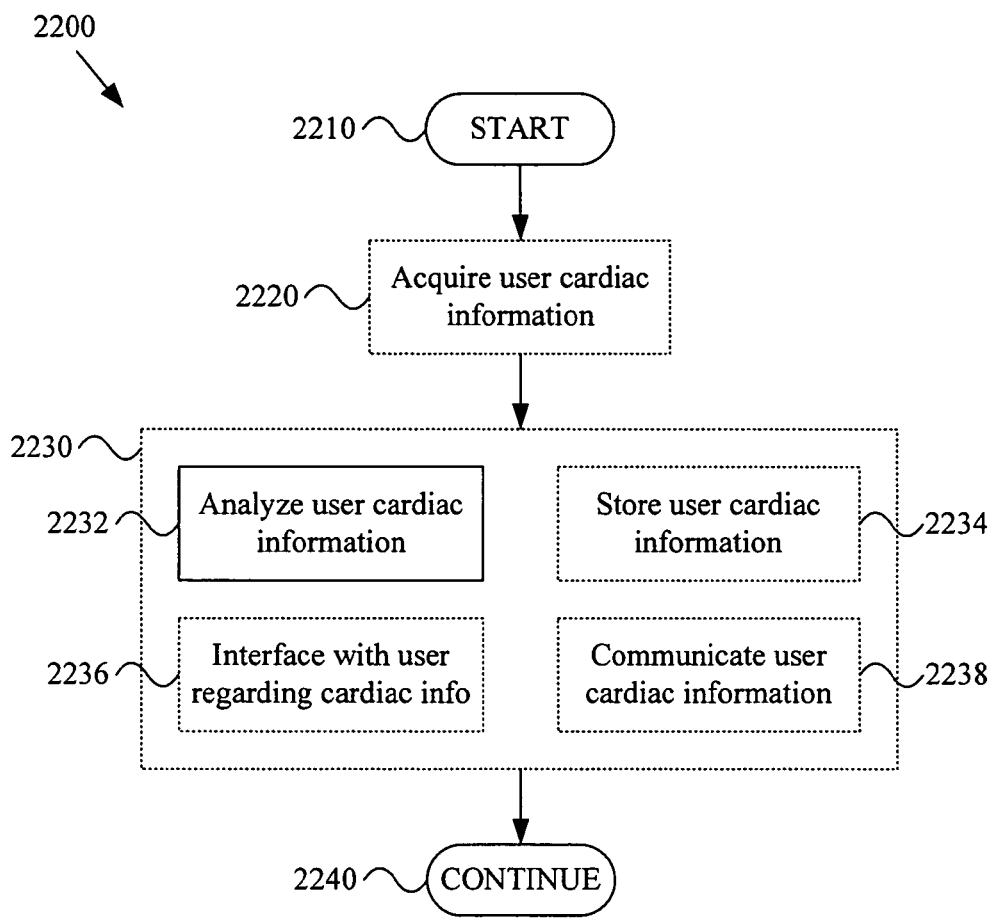
FIG. 22 is a block diagram illustrating an exemplary method, in a mobile communication device or other device, for analyzing cardiac information of a user, in accordance with various aspects of the present invention.

FIG. 22 is a block diagram illustrating an exemplary method 2200, in a mobile communication device (or computing system), for analyzing cardiac information of a user, in accordance with various aspects of the present invention. The exemplary method 2200 may, for example and without limitation, share various functional characteristics with the exemplary mobile communication device 2000 and computer system 2100 illustrated in FIGS. 20-21 and discussed previously.

The exemplary method 2200 may begin executing for any of variety of reasons, some of which were discussed previously with regard to various mobile communication devices and computer systems. The exemplary method 2200 may, at step 2220, comprise acquiring user cardiac information (e.g., from a user of a mobile communication device or general-purpose computer user interface device). Such acquisition was generally discussed previously with regard to various mobile communication devices and computer systems (e.g., various cardiac information acquisition modules and various related modules).

The exemplary method 2200 may, at step 2230, comprise performing various additional functions related to the cardiac information acquired at step 2220. For example and without limitation, step 2232 may comprise analyzing at least a portion of acquired cardiac information. Various characteristics of such analysis were discussed previously and will also be discussed later. Step 2232 may, for example and without limitation, share various functional characteristics with the processing modules 2050, 2150 of the exemplary mobile communication device 2000 and computer system 2100 illustrated in FIGS. 20-21 and discussed previously.

Also for example, step 2234 may comprise storing at least a portion of acquired cardiac information in a memory. Non-limiting examples of such storage were discussed previously with regard to the cardiac information acquisition module 1710 and memory 1740 of the exemplary MCD 1700 of FIG. 17. Further for example, step 2236 may comprise interfacing with a user regarding the acquired cardiac information. Non-limiting examples of such user interaction were discussed previously with regard to the cardiac information acquisition module 1710 and the U/I module 1730 of the exemplary MCD 1700 of FIG. 17. Still further for example, step 2238 may comprise communicating acquired user cardiac information with other communication systems. Various characteristics of such communication will be discussed later.

The exemplary method 2200 may, at step 2240, comprise performing any of a variety of types of continued processing. Such continued processing may, for example, comprise acquiring, communicating and/or analyzing additional cardiac or user information. Various non-limiting examples of such continued processing were presented previously and will also be presented later.

Figure 23:
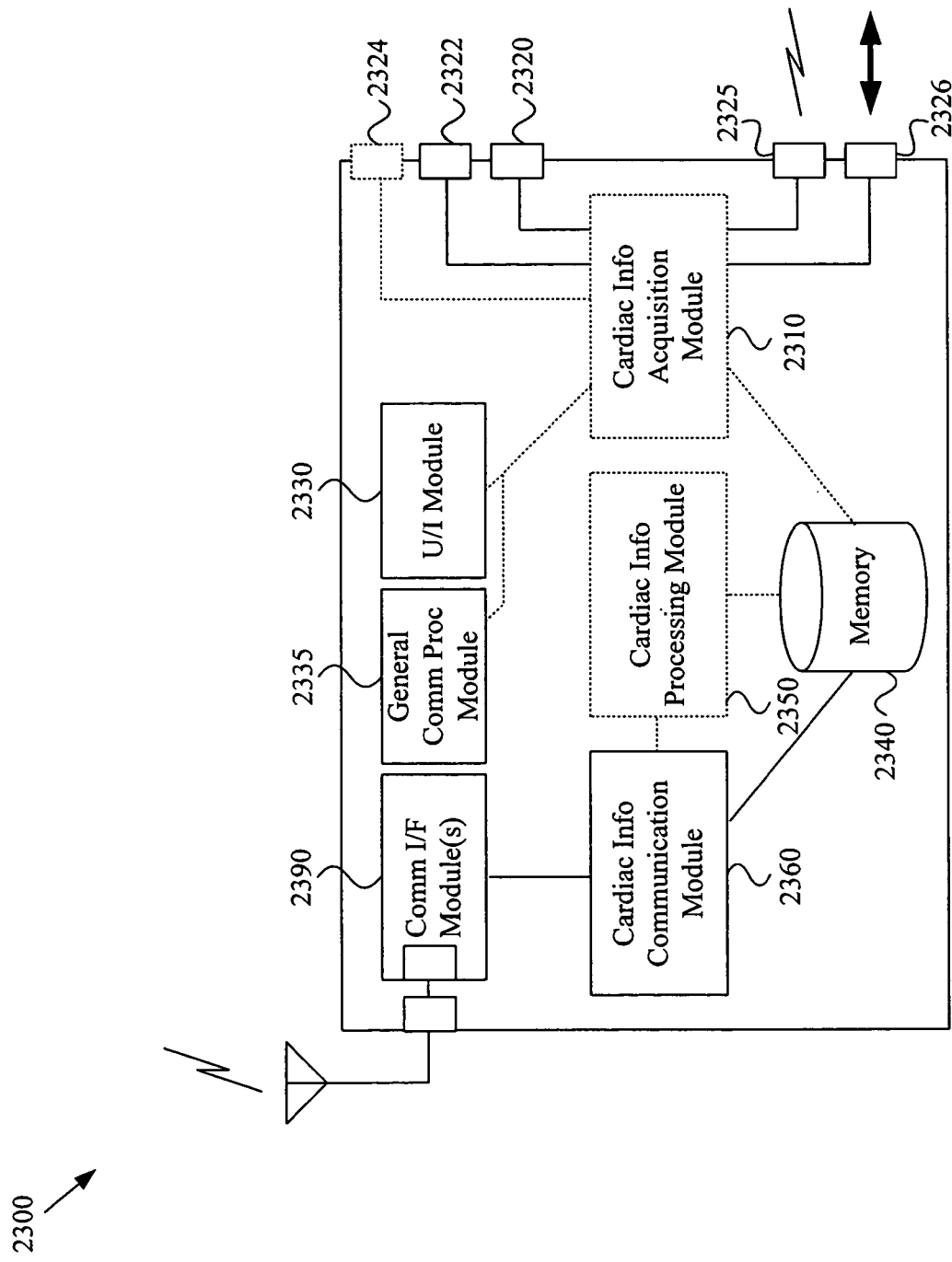
FIG. 23 is a block diagram illustrating various portions of an exemplary mobile communication device, in accordance with various aspects of the present invention.

FIG. 23 is a block diagram illustrating various portions of an exemplary mobile communication device 2300, in accordance with various aspects of the present invention. The exemplary mobile communication device 2300 may, for example and without limitation, share various characteristics with the exemplary mobile communication devices (and portions thereof) illustrated in any of FIGS. 1-22 and discussed previously. For example, the mobile communication device 2300 may comprise characteristics of any of a variety of types of mobile communication devices.

The exemplary mobile communication device 2300 may comprise a communication interface module 2390 that is adapted to communicate with one or more general-purpose mobile communication networks. The communication interface module 2390 may, for example and without limitation, share various characteristics with previously discussed communication interface modules. The exemplary mobile communication device 2300 may also comprise a general communication processing module 2335 and a user interface module 2330, which may, for example, share various characteristics with analogous modules discussed previously.

The exemplary mobile communication device 2300 may also, for example and without limitation, comprise a cardiac information acquisition module 2310 and/or cardiac information processing module 2350, various cardiac sensors (e.g., electrodes or acoustical sensors) 2320, 2322, 2324 and various cardiac communication ports 2325, 2326. As discussed previously with regard to other exemplary communication devices, such modules or components may, for example, be utilized to acquire and/or process (e.g., analyze) cardiac information (e.g., from a user of the mobile communication device 2300. Such modules and/or components are merely one illustration of a manner in which cardiac information may be acquired for analysis by the exemplary mobile communication device 2300.

The exemplary mobile communication device 2300 may additionally, for example, comprise a cardiac information communication module 2360 ("CICM"). The CICM 2360 may communicate cardiac information in any of a variety of manners. The following discussion will present various non-limiting examples of such communication. Note that in various exemplary scenarios, the cardiac information communicated by the CICM 2360 may be stored in the memory 2340.

The CICM 2360 may be adapted to communicate cardiac information over (at least in part) a general-purpose communication network (e.g., a mobile communication network). For example, the CICM 2360 may be adapted to utilize the communication interface module(s) 2390 (and/or the general communication processing module 2335) to perform such communication.

The CICM 2360 may be adapted to determine when to communicate cardiac information. For example and without limitation, the CICM 2360 may be adapted to initiate communication of the cardiac information or may be adapted to respond to an initiating request/command from another source (e.g., from a user of the mobile communication device 2300 or from another communication device). For example, the CICM 2360 may be adapted to communicate the cardiac information in response to a user request (or command) received through the user interface module 2330. Further for example, the CICM 2360 may be adapted to communicate the cardiac information in response to a request (or command) received from another communication device through the communication interface module 2390.

The CICM 2360 may, for example, be adapted to communicate cardiac information in response to the acquisition of cardiac information (e.g., cardiac information obtained by the cardiac information acquisition module 2310). For example, the CICM 2360 may be adapted to immediately communicate acquired cardiac information to another system in real-time or in a time-delayed manner.

Further for example, the CICM 2360 may be adapted to communicate cardiac information in response to analysis of cardiac information (e.g., analysis performed by the cardiac information processing module 2350). In a non-limiting exemplary scenario, the CICM 2360 may be adapted to communicate cardiac information in response to particular analysis results (e.g., exceeding a particular level of health concern). For example, the CICM 2360 may be adapted to automatically and immediately communicate cardiac information when analysis results are indicative of a relatively dangerous health condition. Also for example, the CICM 2360 may be adapted to periodically (e.g., daily) communicate cardiac information when analysis results are indicative of a relatively moderate alert level. Further for example, the CICM 2360 may be adapted to not communicate cardiac information when analysis results are indicative of a relatively normal or safe cardiac condition.

The CICM 2360 may, for example, be adapted to communicate cardiac information based, at least in part, on a profile comprising information indicating when (and/or how) such communication should occur. For example and without imitation, such a profile may comprise information indicating various conditions under which cardiac information should be communicated (e.g., timing conditions, analysis result conditions, user interaction conditions, etc.).

In general, the CICM 2360 may be adapted to communicate cardiac information in response to any of a variety of causes or conditions. Accordingly, the scope of various aspects of the present invention should not be limited by characteristics of any particular causes or conditions.

The CICM 2360 may be adapted to communicate any of a variety of types of cardiac information. For example, the CICM 2360 may be adapted to communicate cardiac information acquired from a user of the mobile communication device 2300 (e.g., in real-time or stored cardiac information). Also for example, the CICM 2360 may be adapted to communicate cardiac information acquired by the mobile communication device 2300 during a plurality of cardiac information acquisition events (or acquisition periods). The CICM 2360 may, for example, be adapted to communicate all or a portion of acquired cardiac information. The CICM 2360 may also, for example, be adapted to communicate a summary of acquired cardiac information and/or analysis results of acquired cardiac information. Such summary or analysis results may, for example, comprise a summary or analysis results corresponding to a single event of cardiac information acquisition or a plurality of such events spaced in time. Communicated cardiac information may comprise various other types of information (e.g., location information (e.g., obtained through GPS, cell triangulation, UWB, network location, etc.), user identification information, care provider information, medical history information, insurance information, contact information, etc.). The scope of various aspects of the present invention should not be limited by characteristics of particular types of cardiac or cardiac-related information that might be communicated.

The CICM 2360 may be adapted to communicate the cardiac information in any of a variety of manners (e.g., utilizing the communication interface module 2390 and/or general communication processing module 2335). For example and without limitation, the CICM 2360 may be adapted to communicate the cardiac information through a cellular telephone network. Also for example, the CICM 2360 may be adapted to communicate the cardiac information through a computer network (e.g., a PAN, LAN, WAN, MAN, the Internet, etc.). Further for example, the CICM 2360 may be adapted to communicate the cardiac information through a television network, telephone network, and/or a satellite communication network.

The CICM 2360 may be adapted to communicate the cardiac information utilizing any of a variety of communication protocols. For example and without limitation, the CICM 2360 may be adapted to communicate the cardiac information (e.g., through the communication interface module 2390) utilizing a cellular telephone protocol (e.g., GSM, EDGE, CDMA, WCDMA, etc.). Also for example, the CICM 2360 may be adapted to communicate the cardiac information (e.g., through the communication interface module 2390) utilizing a computer communication protocol (e.g., Bluetooth, IEEE 802.11, UltraWideBand, IEEE 802.15, Ethernet, Token Ring, USB, FireWire, etc.). Further for example, the CICM 2360 may be adapted to communicate the cardiac information utilizing a communication protocol (or a portion thereof) that is customized for the communication of cardiac or health-related information. The scope of various aspects of the present invention should not be limited by characteristics of any particular manner of communicating cardiac information (e.g., communication network characteristics or communication protocol characteristics).

The CICM 2360 may, for example, be adapted to interact with a user of the mobile communication device 2300 regarding the communication of cardiac information in any of a variety of manners. For example, the CICM 2360 may be adapted to communicate the cardiac information without any interaction (e.g., real-time interaction) with the user. In such an exemplary scenario, a user might not be aware that such communication is occurring. Also for example, the CICM 2360 may be adapted to interact with a user regarding the communication of cardiac information (e.g., notifying the user of the communication and/or verifying with the user that the communication of such information should proceed). The scope of various aspects of the present invention should not be limited by characteristics of any particular type of user interaction or the existence of non-existence of such user interaction.

The CICM 2360 may be adapted to communicate the cardiac information to any of a variety of destinations. For example and without limitation, the CICM 2360 may be adapted to communicate the cardiac information to a destination associated with medical care (e.g., a care facility, hospital room, emergency room, physician, etc.). Also for example, the CICM 2360 may be adapted to communicate the cardiac information to a destination associated with emergency assistance (e.g., "911," ambulance service, police department, fire department, paramedics, etc.). Further for example, the CICM 2360 may be adapted to communicate the cardiac information to a destination (e.g., a virtual cardiac service) comprising an organization dedicated to handling such cardiac information. Still further for example, the CICM 2360 may be adapted to communicate the cardiac information to other destinations that may have an interest in such information (e.g., insurers, employers, personal assistants, particular family members, etc.).

The destination(s) for communicated cardiac information may be specified by a user (e.g., in a communication profile established by the user). Note that in various exemplary scenarios, the communication of cardiac information may be governed by personal privacy considerations. For example, the communication of various types of cardiac information may be governed by the Health Information Protection Act ("HIPA"). In other exemplary scenarios, the CICM 2360 may be adapted to encrypt, or otherwise securely communicate, various types of cardiac or personal information. In still other exemplary scenarios, the CICM 2360 may be adapted to disassociate communicated cardiac information from a particular user's identity. The scope of various aspects of the present invention should not be limited by characteristics of any particular destination for communicated cardiac or cardiac-related information.

The CICM 2360 may be adapted to perform any of a variety of additional functions (e.g., functions that may be logically associated with the communication of cardiac information). For example and without limitation, the CICM 2360 may be adapted to establish and maintain a communication link over which the user may communicate to various entities regarding communicated cardiac information. Also for example, the CICM 2360 may be adapted to obtain additional information from the user (e.g., from the memory 2340 or through the user interface module 2330). Further for example, the CICM 2360 may be adapted to obtain instructions for the user (e.g., behavior instructions) and present such obtained instructions to the user (e.g., utilizing the user interface module 2330). The scope of various aspects of the present invention should not be limited by characteristics of any particular additional functions related to the communication of cardiac information that might be performed.

The previous exemplary mobile communication device 2300 was presented to provide specific illustrations of various generally broader aspects of the present invention. Various aspects of the present invention may be applied to other electronic devices. For example and without limitation, a general-purpose computer may be adapted to communicate cardiac information.

Figure 24:
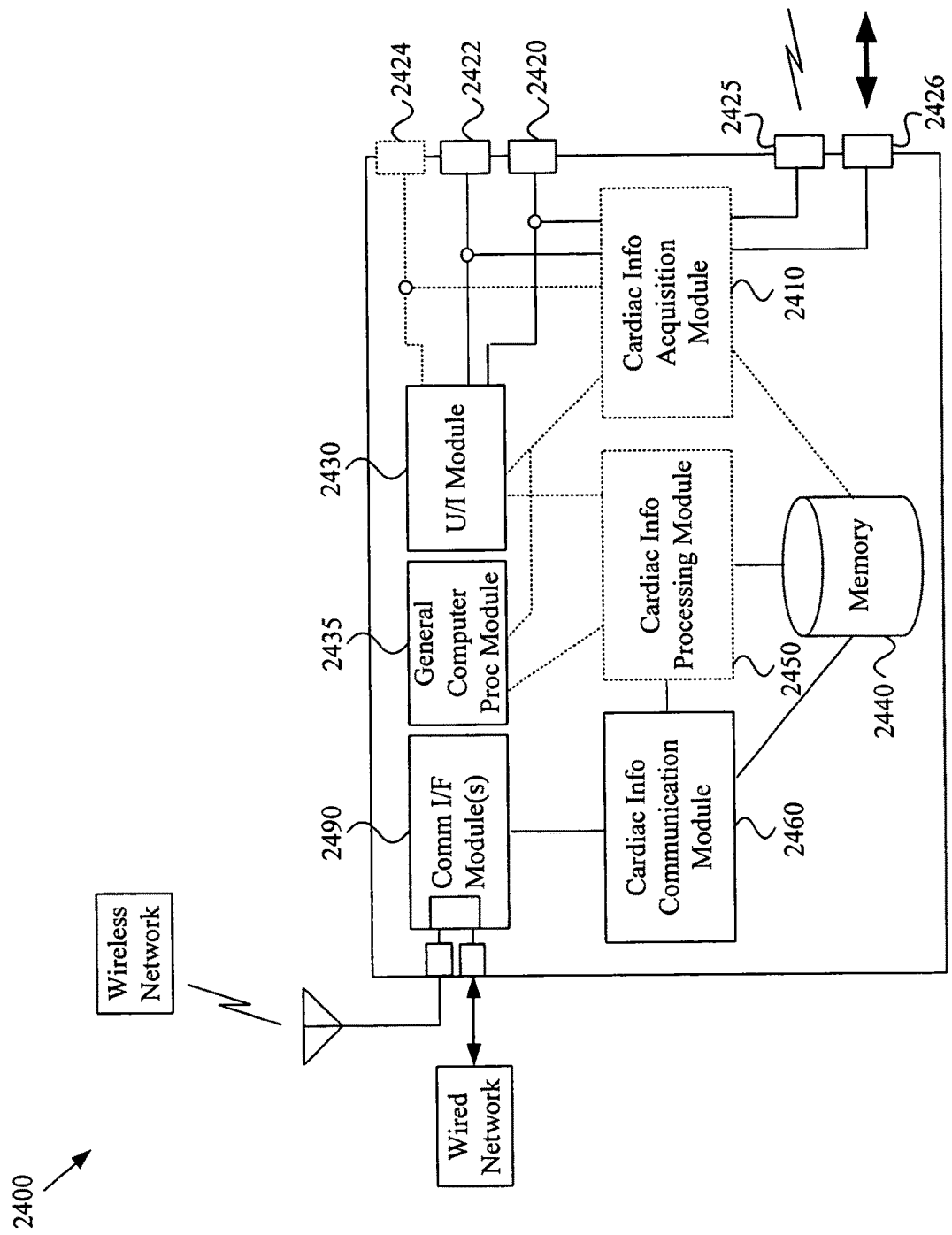
FIG. 24 is a block diagram illustrating various portions of an exemplary computer system, in accordance with various aspects of the present invention.

FIG. 24 is a block diagram illustrating various portions of an exemplary computer system 2400, in accordance with various aspects of the present invention. The exemplary computer system 2400 may, for example and without limitation, share various characteristics with exemplary computer systems and/or associated components discussed previously and illustrated in any of FIGS. 1-23. The exemplary computer system 2400 may, for example comprise various interfaces to a general-purpose computer user interface device (various examples of which were presented previously). Such interfaces may, for example and without limitation, comprise a source of cardiac information, which may be communicated by the cardiac information communication module 2460 ("CICM"). Such interfaces may also, for example, comprise a source of cardiac information, which may be processed by the exemplary computer system 2400 (e.g., by the cardiac information processing module 2450), resulting in related cardiac information, which may be communicated by the CICM 2460.

The exemplary computer system 2400 may comprise characteristics of any of a variety of types of computer systems. For example and without limitation, the exemplary computer system 2400 may comprise characteristics of a mobile computer and/or a desktop computer. Also for example, the computer system 2400 may comprise characteristics of a laptop computer, notebook computer and/or handheld computer.

The following discussion will generally be directed to the CICM 2460 of the exemplary computer system 2400. The CICM 2460 of the exemplary computer system 2400 may, for example and without limitation, share various characteristics with the CICM 2360 of the mobile communication device 2300 illustrated in FIG. 23 and discussed previously. The CICM 2460 may, for example, be adapted to communicate cardiac information obtained from a user of the computer system 2400. Also for example, the CICM 2460 may be adapted to communicate a summary of cardiac information obtained from the user and/or results of analysis of cardiac information obtained from the user (e.g., as performed by the cardiac information processing module 2450).

As discussed previously with regard to the CICM 2360 of the exemplary mobile communication device 2300 illustrated in FIG. 23, the CICM 2460 may, for example, be adapted to communicate cardiac information obtained from a user of the computer system 2400 over a computer communication network. Such cardiac information may, for example, be obtained through the cardiac information acquisition module 2410 and communicated utilizing the communication interface module 2490.

As discussed previously with regard to the CICM 2360 of the exemplary mobile communication device 2300 illustrated in FIG. 23, the CICM 2460 may, for example, be adapted to initiate communication of the cardiac information in response to an initiating request (or command) from another entity (e.g., a user or another communication system). The CICM 2460 may also, for example, be adapted to initiate communication of the cardiac information in response to analysis of the cardiac information.

Also for example, the cardiac information may comprise characteristics of any of a variety of cardiac or cardiac-related information. For example, the cardiac information may comprise raw or processed cardiac data, cardiac information analysis results, user identification information, location information, care provider information, physician information, medical history information, insurance information, etc.

As discussed previously with regard to the CICM 2360 of the mobile communication device 2300 illustrated in FIG. 23, the CICM 2460 may be adapted to communicate the cardiac information in any of a variety of manners. For example and without limitation, the CICM 2460 may be adapted to communicate the cardiac information through any of a variety of communication networks and utilizing any of a variety of communication protocols (e.g., standard, proprietary, customized, etc.).

Also as discussed previously with regard to the CICM 2360 of the mobile communication device 2300 illustrated in FIG. 23, the CICM 2460 may be adapted to interact with a user in any of a variety of manners. For example and without limitation, the CICM 2460 may be adapted to communicate with a user (e.g., utilizing the user interface module 2430) regarding the communication of the cardiac information, the results of such communication, information received in response to such a communication (e.g., user behavior instructions), etc.

Figure 25:
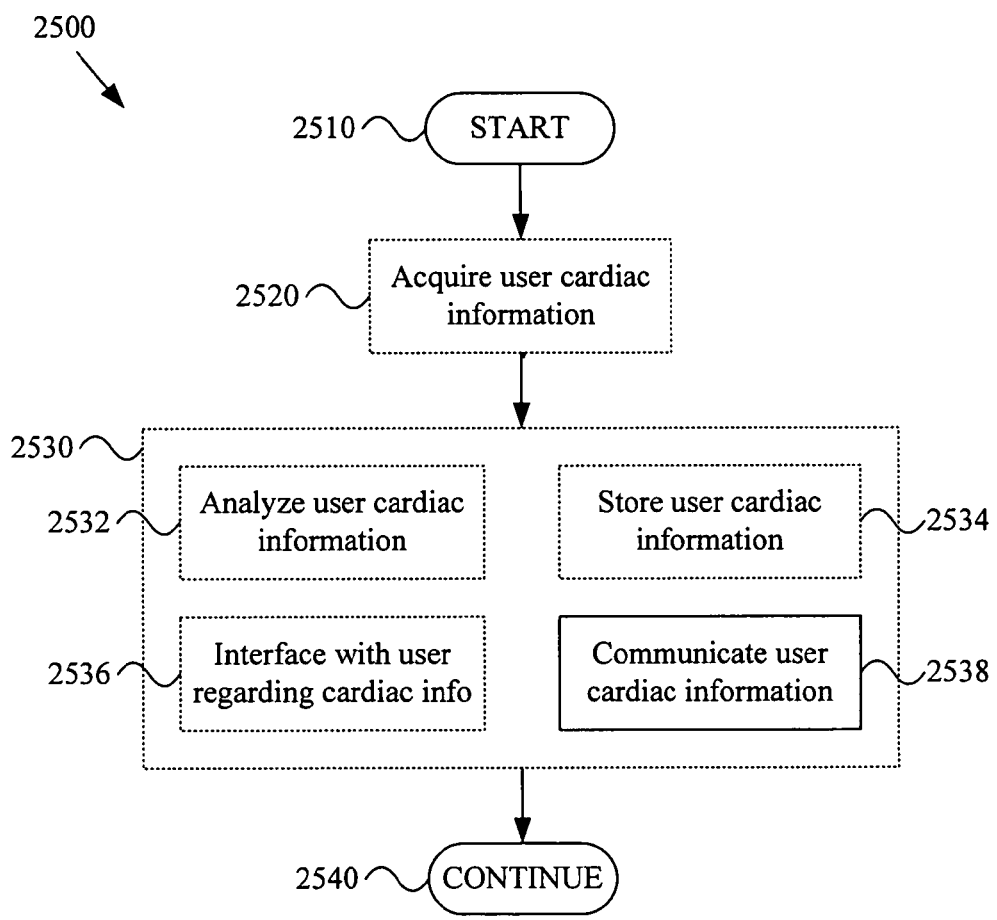
FIG. 25 is a block diagram illustrating an exemplary method, in portable communication device or other device, for communicating cardiac information, in accordance with various aspects of the present invention.

FIG. 25 is a block diagram illustrating an exemplary method 2500, in a mobile communication device (or computing system), for analyzing cardiac information of a user, in accordance with various aspects of the present invention. The exemplary method 2500 may, for example and without limitation, share various functional characteristics with the exemplary mobile communication device 2300 and computer system 2400 illustrated in FIGS. 23-24 and discussed previously.

The exemplary method 2500 may start at 2510 for any of variety of reasons, some of which were discussed previously with regard to various mobile communication devices and computer systems. The exemplary method 2500 may, at step 2520, comprise acquiring user cardiac information (e.g., from a user of a mobile communication device or general-purpose computer user interface device). Such acquisition was generally discussed previously with regard to various mobile communication devices and computer systems (e.g., various cardiac information acquisition modules and various related modules).

The exemplary method 2500 may, at step 2530, comprise performing various additional functions related to the cardiac information acquired at step 2520. For example and without limitation, step 2538 may comprise communicating at least a portion of acquired cardiac information (or information resulting from analysis thereof). Various characteristics of such analysis will be discussed later. Step 2538 may, for example and without limitation, share various functional characteristics with the cardiac information communication modules 2360, 2460 of the exemplary mobile communication device 2300 and computer system 2400 illustrated in FIGS. 23-24 and discussed previously.

Also for example, step 2534 may comprise storing at least a portion of acquired cardiac information in a memory. Non-limiting examples of such storage were discussed previously with regard to the cardiac information acquisition module 1710 and memory 1740 of the exemplary MCD of FIG. 17. Further for example, step 2536 may comprise interfacing with a user regarding the acquired cardiac information. Non-limiting examples of such user interaction were discussed previously with regard to the cardiac information acquisition module 1710 and the U/I module 1730 of the exemplary MCD of FIG. 17. Still further for example, step 2536 may comprise analyzing acquired user cardiac information. Non-limiting examples of such analysis were discussed previously with regard to the cardiac information processing modules 2050, 2150 of the exemplary mobile communication device 2000 and computer system 2100 illustrated in FIGS. 20-21.

The exemplary method 2500 may, at step 2540, comprise performing any of a variety of continued processing. Such continued processing may, for example, comprise acquiring, communicating and/or analyzing additional cardiac information. Various non-limiting examples of such continued processing were presented previously.

Figure 26:
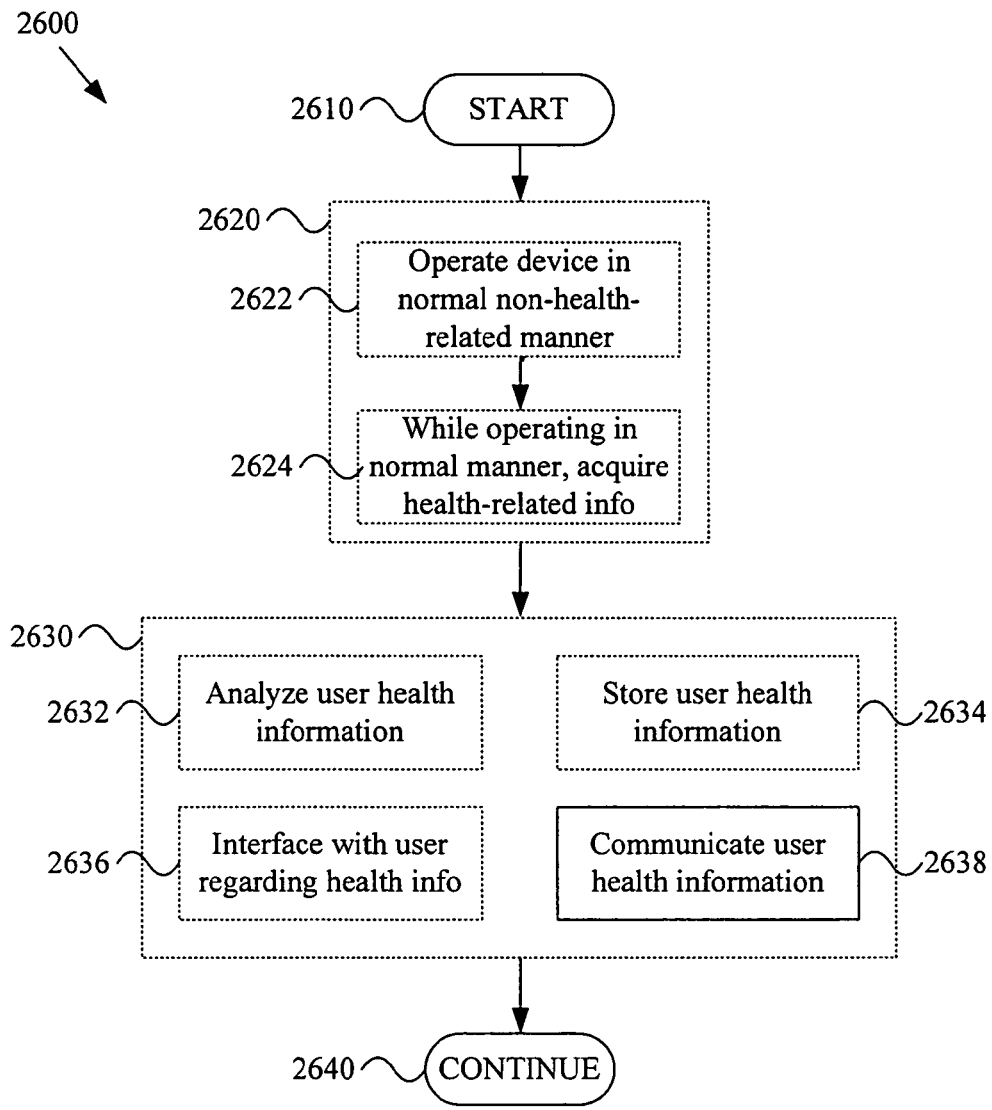
FIG. 26 is a block diagram illustrating an exemplary method, in an electronic device, for communicating cardiac information, in accordance with various aspects of the present invention.

FIG. 26 is a block diagram illustrating an exemplary method 2600, in an electronic device, for communicating cardiac information, in accordance with various aspects of the present invention. The exemplary method 2600 may, for example and without limitation, share various characteristics with exemplary methods illustrated in any of FIGS. 1-25 and discussed previously.

The exemplary method 2600 may be implemented in any of a large variety of electronic devices (e.g., electronic devices that are not normally associated with user health activities). For example and without limitation, such an electronic device may comprise characteristics of various general-purpose communication devices, computing devices, entertainment devices, audio/visual devices, standard household devices, etc. Also for example, such electronic devices might not generally include electronic devices substantially dedicated to health-monitoring, such as might typically be found in health care facilities, health clubs, etc. During such use, the exemplary method 2600 may advantageously and without limitation provide for monitoring of user health when such health is not on the user's mind. In other words, the exemplary method 2600 may, among other things, provide for monitoring user health without interrupting a user's normal routine. As a non-limiting example, the exemplary method 2600 may provide for monitoring user health during work or commuting, rather than solely during exercise or focused medical activities.

The exemplary method 2600 may begin executing at step 2610 for any of a large variety of reasons. The exemplary method 2600 may, at step 2620, comprise acquiring health-related information from a user of the electronic device implementing the exemplary method 2600. For example, the exemplary method 2600 may, at step 2622, comprise performing normal operation of the electronic device, where such normal use is not generally associated with user health.

The exemplary method 2600 may then, at step 2624, comprise, while performing normal operation at step 2622, acquiring health-related information of a user of the electronic device. Step 2624 may comprise acquiring such health-related information in any of a variety of manners. For example and without limitation, step 2624 may comprise monitoring cardiac activity of the user, monitoring electrical characteristics of the user, monitoring audio characteristics of the user, monitoring visual characteristics of the user, etc. For example and without limitation, step 2624 may comprise performing such acquisition substantially without the user's awareness that such acquisition is occurring. Though not necessary, such covert health information acquisition may advantageously provide for an accurate representation of a user's normal state of health (e.g., avoiding white jacket syndrome and other effects associated with utilizing dedicated health equipment or working directly with health care professionals). Many non-limiting exemplary characteristics of such information acquisition were presented previously.

The exemplary method 2600 may, at step 2630, comprise performing any of a variety of activities related to the information acquired at step 2620. For example, step 2632 may comprise analyzing the acquired health information, step 2634 may comprise storing acquired health information (e.g., for longer than a transient period), step 2636 may comprise interfacing with the user regarding acquired health information, and step 2628 may comprise communicating acquired health information to another electronic device or system. Many non-limiting exemplary characteristics of such analysis, storage, user interfacing and communicating were presented previously.

Figure 27:
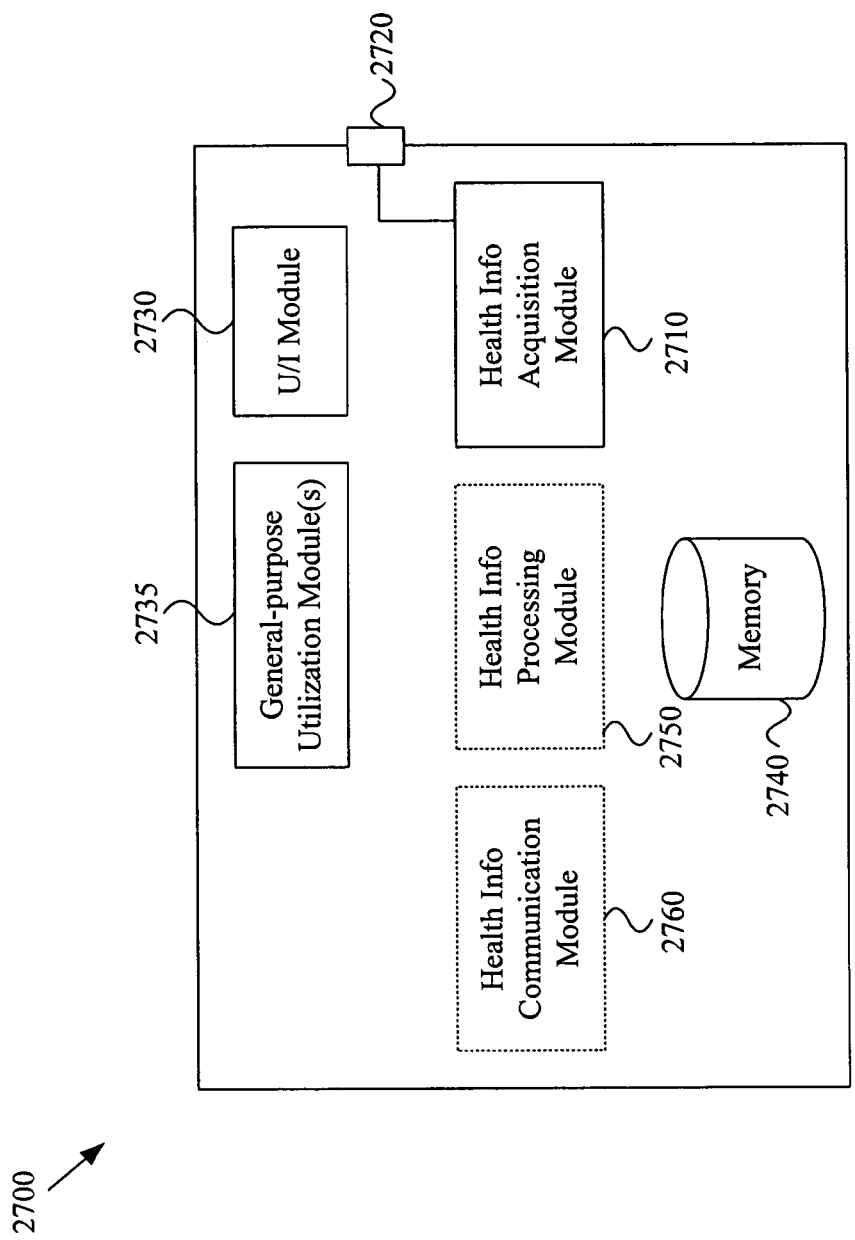
FIG. 27 is a block diagram illustrating various portions of an exemplary electronic device, in accordance with various aspects of the present invention.

FIG. 27 is a block diagram illustrating various portions of an exemplary electronic device 2700, in accordance with various aspects of the present invention. The exemplary electronic device 2700 may, for example and without limitation, share various characteristics with the exemplary mobile communication devices (or portions thereof) or computer systems (or portions thereof) illustrated in any of FIGS. 1-25 and discussed previously. Additionally, the exemplary electronic device 2700 may share various functional characteristics with the exemplary method 2600 illustrated in FIG. 26 and discussed previously.

The exemplary electronic device 2700 may comprise characteristics of any of a large variety of electronic devices (e.g., electronic devices that are not normally associated with user health activities). For example and without limitation, the electronic device 2700 may comprise characteristics of communication devices, computing devices, entertainment devices, audio/visual devices, standard household devices, etc. Also for example, the electronic device might generally not include electronic devices substantially dedicated to health-monitoring, such as might typically be found in health care facilities, health clubs, etc.

The exemplary electronic device 2700 may comprise one or more general-purpose utilization modules 2735 that the electronic device 2700 utilizes for its normal non-health-related operation. The exemplary electronic device 2700 may also comprise a health information acquisition module 2710. The acquisition module 2710 may, for example and without limitation, share various functional characteristics with step 2620 of the exemplary method 2600 illustrated in FIG. 26 and discussed previously.

The acquisition module 2710 may, for example, be adapted to (e.g., while the general-purpose utilization module(s) 2735 is operating normally) acquire health-related information of a user of the electronic device 2700. The acquisition module 2710 may be adapted to acquire such health-related information in any of a variety of manners. For example and without limitation, the acquisition module 2710 may be adapted to monitor cardiac activity of the user, monitor electrical characteristics of the user, monitor audio characteristics of the user, monitor visual characteristics of the user, monitor temperature characteristics of the user, etc. For example, the acquisition module 2710 may be adapted to utilize any of a variety of sensors 2720 (and/or communication ports) for such acquisition. For example and without limitation, the acquisition module 2710 may be adapted to perform such acquisition substantially without the user's awareness that such acquisition is occurring. Many non-limiting exemplary characteristics of such information acquisition were presented previously.

The exemplary electronic device 2700 may also comprise any of a variety of modules to perform additional activities corresponding to acquired health-related information. For example, the exemplary electronic device 2700 may comprise any of: a health-information processing module 2750 adapted to analyze acquired health information, a memory 2740 adapted to store acquired health information (e.g., for longer than a transient period), a user interface module 2730 adapted to interface with a user regarding acquired health information, and a health-information communication module 2760 adapted to communicate acquired and/or analyzed health information to another electronic device or system (e.g., utilizing dedicated communication circuitry or utilizing communication circuitry inherent in the electronic device 2700). Many non-limiting exemplary characteristics of such analysis, storage, user interfacing and communicating were presented previously.

Various aspects of the present invention may be implemented in various degrees of integration. For example, various modules may be integrated in an independent integrated circuit or may be integrated into other integrated circuits. For example and without limitation, various modules discussed herein may be integrated into a baseband processor chip or controller chip. Accordingly, the scope of various aspects of the present invention should not be limited by characteristics of any particular degree of integration.

Various aspects of the present invention were illustrated by referring to various functional modules. It should be noted that such modules may be implemented in hardware, software or a combination thereof. Additionally, various modules may share various submodules or subcomponents. For example, a first module and a second module may share a particular hardware component or software submodule. Accordingly, the scope of various aspects of the present invention should not be limited by characteristics of any particular type of module or by any arbitrary boundary between modules.

Further, various functional modules have been described herein utilizing the terminology "adapted to" when referring to functionality that the various functional modules might perform when operational. Thus, the phrase "adapted to", as used herein, is generally synonymous with "capable of", "operational to" and "configured to".

While the invention has been described with reference to certain aspects and embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system comprising:
   a communication interface adapted to wirelessly communicate with a mobile communication device ("MCD");
   a touch screen display operational by a user to utilize the MCD for general communication;
   and a cardiac information acquisition module operational to acquire cardiac information from the user of the MCD, via a cardiac sensor, in response to detecting that the user is utilizing the MCD for a voice call, and wherein the acquisition of the cardiac information from the user of the MCD is covert;
   further wherein the MCD is located in a vehicle;
   and wherein the cardiac sensor comprises one or more electrodes on a steering wheel of the vehicle.

2. The system of claim 1, wherein the MCD comprises a general-purpose mobile e-mail device.

3. The system of claim 1, wherein the cardiac sensor comprises:
   a first electrode coupled to the cardiac information acquisition module; and
   a second electrode coupled to the cardiac information acquisition module, wherein the cardiac information acquisition module is further operational to detect cardiac activity of a user of the MCD.

4. The system of claim 1, wherein the cardiac information acquisition module is operational to interface with memory disposed on the MCD.

5. The system of claim 1, wherein the cardiac information acquisition module is operational to acquire cardiac information from a user of the MCD in response to a use of the MCD.

6. The system of claim 1, wherein the cardiac information acquisition module is operational to periodically acquire cardiac information from a user of the MCD.

7. The system of claim 1, wherein the cardiac information acquisition module is operational to acquire cardiac information from a user of the MCD in response to a command from the user for the MCD to acquire the cardiac information.

8. The system of claim 1, wherein the touch screen display is operational to present information related to acquired cardiac information to a user of the MCD.

9. The system of claim 1, wherein a processor is operational to analyze at least a portion of cardiac information acquired from a user of the MCD.

10. The system of claim 1, wherein a processor is operational to analyze the acquired cardiac information by, at least in part, comparing a primary component of a cardiac signal to a primary component characteristic associated with a known cardiac pathology.

11. The system of claim 1, wherein a processor is operational to analyze the acquired cardiac information by, at least in part:
    determining a difference between a current cardiac signal and at least one previous cardiac signal; and
    determining the existence of a cardiac pathology based, at least in part, on the determined difference.

12. The system of claim 1, wherein the touch screen display is operational to generate an alert message based, at least in part, on cardiac information acquired by the cardiac information acquisition module and analyzed by a processor.

13. The system of claim 1, wherein the communication interface is operational to communicate particular information related to acquired cardiac information over the general-purpose communication network.

14. The system of claim 13, wherein a processor is operational to determine whether to communicate the particular information in response to a request to communicate the particular information.

15. The system of claim 13, wherein the particular information comprises at least a portion of cardiac information acquired by the cardiac information acquisition module.

16. The system of claim 13, wherein the particular information comprises information related to cardiac information acquired by the cardiac information acquisition module and analyzed by a processor.

17. The system of claim 13, wherein the communication interface is operational to communicate the particular information with a destination associated with medical care.

* * * * *